United States Patent
Wallach et al.

(10) Patent No.: US 10,085,926 B2
(45) Date of Patent: Oct. 2, 2018

(54) NAIL POLISH REMOVER COMPOSITIONS AND METHODS

(71) Applicant: Anise Cosmetics, LLC, Collierville, TN (US)

(72) Inventors: Neal Kevin Wallach, Collierville, TN (US); Scott Hofmann, Plantation, FL (US); Tam Tran, Collierville, TN (US)

(73) Assignee: Anise Cosmetics, LLC, Collierville, TN (US)

(*) Notice: Subject to any disclaimer, the term of this patent is extended or adjusted under 35 U.S.C. 154(b) by 0 days.

(21) Appl. No.: 15/645,958

(22) Filed: Jul. 10, 2017

(65) Prior Publication Data
US 2018/0207075 A1    Jul. 26, 2018

Related U.S. Application Data

(60) Provisional application No. 62/507,030, filed on May 16, 2017, provisional application No. 62/451,022, filed on Jan. 26, 2017.

(51) Int. Cl.
*A61K 8/00* (2006.01)
*A61K 8/49* (2006.01)
(Continued)

(52) U.S. Cl.
CPC ............ *A61K 8/4973* (2013.01); *A61K 8/046* (2013.01); *A61K 8/19* (2013.01); *A61K 8/35* (2013.01);
(Continued)

(58) Field of Classification Search
CPC ............. A61K 8/046; A61K 8/19; A61K 8/35
See application file for complete search history.

(56) References Cited

U.S. PATENT DOCUMENTS 5,258,070 A    11/1993    Monteleone et al.
5,346,652 A    9/1994    Dotolo et al.
(Continued)

FOREIGN PATENT DOCUMENTS

CN    102641221 A    8/2012
EP    0009691 A1    4/1980
(Continued)

OTHER PUBLICATIONS

"Acetone-free nail polish removing composition," An IP.com Prior Art Database Technical Disclosure: IP.com No. IPCOM000238762D, published Sep. 17, 2014. (2 pages).
(Continued)

*Primary Examiner* — Mark Eashoo
*Assistant Examiner* — M. Reza Asdjodi
(74) *Attorney, Agent, or Firm* — Fish & Richardson P.C.

(57) ABSTRACT

Methods, systems, and apparatus, including computer programs encoded on computer storage media, for a row-level security. One of the methods includes receiving a request for one or more objects. The method includes determining that a type of the one or more requested objects is associated with an object representative of instance level security. The method includes determining access is authorized to at least some of the one or more objects. Determining access includes obtaining a first access statement associated with the type of the one or more objects, obtaining a second access statement associated with the object representative of instance level security, combining at least the first access statement and the second access statement into a third access statement, and obtaining one or more objects using the third access statement. The method also includes providing the authorized subset of objects to the user.

16 Claims, 8 Drawing Sheets
(Continued)

(7 of 8 Drawing Sheet(s) Filed in Color)

(51) Int. Cl.
    *A61K 8/04*     (2006.01)
    *A61Q 3/04*     (2006.01)
    *A61K 8/37*     (2006.01)
    *A61K 8/35*     (2006.01)
    *A61K 8/19*     (2006.01)
    *A61K 8/92*     (2006.01)
    *A61K 8/73*     (2006.01)
    *A61K 8/65*     (2006.01)

(52) U.S. Cl.
    CPC .................. *A61K 8/37* (2013.01); *A61K 8/65*
    (2013.01); *A61K 8/735* (2013.01); *A61K 8/922*
    (2013.01); *A61Q 3/04* (2013.01)

(56) References Cited

U.S. PATENT DOCUMENTS

| | | | | |
|---|---|---|---|---|
| 5,372,742 | A | | 12/1994 | Bayless |
| 5,486,305 | A | * | 1/1996 | Faryniarz ................. A61K 8/37 106/311 |
| 5,827,807 | A | * | 10/1998 | Aoshima ................. A61K 8/35 134/38 |
| 6,187,299 | B1 | * | 2/2001 | Wimmer ................. A61K 8/03 424/401 |
| 6,420,327 | B1 | * | 7/2002 | Machac, Jr. ............. C09D 9/00 134/38 |
| 6,479,445 | B1 | * | 11/2002 | Machac, Jr. ............. C09D 9/00 134/38 |
| 6,787,127 | B2 | * | 9/2004 | DiGiulio ................. A61K 8/42 424/400 |
| 6,958,148 | B1 | * | 10/2005 | Green ..................... A61K 8/11 424/401 |
| 8,961,680 | B2 | | 2/2015 | Pasin et al. |
| 9,434,843 | B1 | * | 9/2016 | Heiman .................... B43L 1/00 |
| 2002/0086039 | A1 | * | 7/2002 | Lee .......................... A61K 8/22 424/401 |
| 2004/0028640 | A1 | * | 2/2004 | Arnaud .................... A61K 8/37 424/70.31 |
| 2004/0142830 | A1 | * | 7/2004 | Tavares ..................... A61K 8/37 510/118 |
| 2004/0180027 | A1 | * | 9/2004 | Kumar ................... A61K 8/0212 424/70.14 |
| 2005/0058689 | A1 | * | 3/2005 | McDaniel ................ A01N 37/46 424/426 |
| 2006/0089281 | A1 | * | 4/2006 | Gibson .................... C09D 9/005 510/201 |
| 2008/0241371 | A1 | * | 10/2008 | Havelka ................. C09D 5/008 427/154 |
| 2010/0178262 | A1 | * | 7/2010 | Kergosien .............. A61K 8/361 424/61 |
| 2011/0229424 | A1 | * | 9/2011 | Schumann ................ A61K 8/06 424/62 |
| 2011/0274643 | A1 | * | 11/2011 | Yontz ....................... A61K 8/25 424/76.1 |
| 2012/0175562 | A1 | | 7/2012 | Howard et al. |
| 2012/0259049 | A1 | * | 10/2012 | Donate .................. C09D 7/001 524/290 |
| 2013/0319462 | A1 | * | 12/2013 | Cifelli ..................... A61Q 3/04 134/6 |
| 2014/0147395 | A1 | * | 5/2014 | Rieth ...................... C11B 9/008 424/49 |
| 2014/0255326 | A1 | * | 9/2014 | Pasin ..................... C09D 7/001 424/61 |
| 2015/0159028 | A1 | | 6/2015 | Pasin et al. |
| 2015/0252302 | A1 | * | 9/2015 | Rieth .................... C11D 3/2072 514/772 |

FOREIGN PATENT DOCUMENTS

| | | | |
|---|---|---|---|
| EP | 1591101 A1 | 11/2005 | |
| FR | 2645417 A3 * | 10/1990 | ........... A45D 29/007 |
| GB | 977906 A | 12/1964 | |
| GB | 2403480 A * | 1/2005 | ............... A61K 8/35 |
| JP | H06001710 A | 1/1994 | |
| JP | 3364768 B2 | 1/1995 | |
| JP | H08268842 A | 10/1996 | |
| JP | 3005599 B2 | 1/2000 | |
| JP | 2000095646 A | 4/2000 | |
| JP | 2000319134 A | 11/2000 | |
| JP | 2003137735 A | 5/2003 | |
| JP | 2004331522 A | 11/2004 | |
| JP | 2009209084 A | 9/2009 | |
| JP | 2009256242 A | 11/2009 | |
| JP | 2013241362 A | 12/2013 | |
| JP | 5484624 B1 | 5/2014 | |
| KR | 0118864 B1 | 10/1997 | |
| RU | 2502502 C1 | 12/2013 | |
| WO | WO 2006/013200 A1 | 2/2006 | |
| WO | WO 2009/016064 A1 | 2/2009 | |

OTHER PUBLICATIONS

Derwent English language fields for Mexican Appl No. MXPA2006009688A, published Feb. 25, 2008. (2 pages).
International Search Report and Written Opinion for corresponding PCT Appl No. PCT/US2018/015162, dated Jun. 11, 2018.

* cited by examiner

1. Valve
2. Bemis High-Barrier Bag
3. Product
4. Propellant
5. Actuator (Dispenser)
6. Can

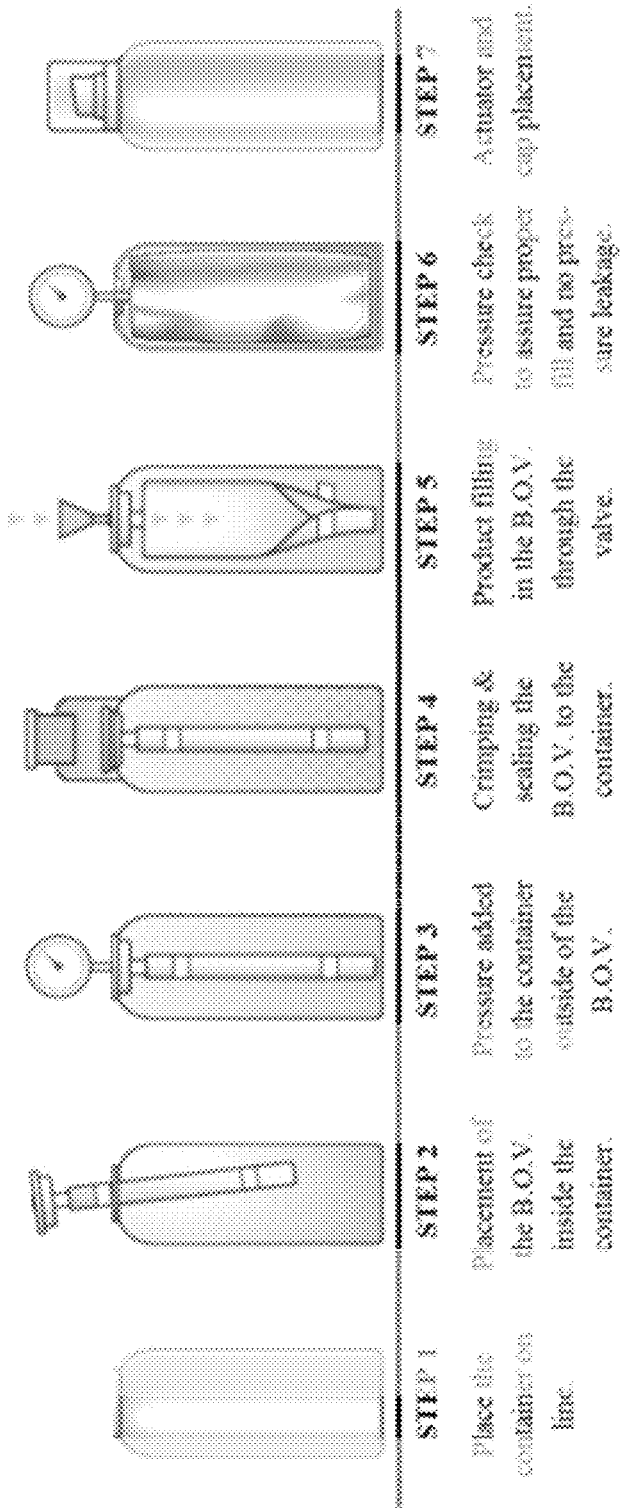

NAIL POLISH REMOVER COMPOSITIONS AND METHODS

CROSS-REFERENCE TO RELATED APPLICATIONS

This application claims priority under 35 U.S.C. § 119(e)(1) to U.S. Provisional Application Nos. 62/507,030, filed May 16, 2017 and 62/451,022, filed Jan. 26, 2017. The contents of both of these applications are hereby incorporated by reference in their entirety.

TECHNICAL FIELD

This disclosure relates to solvent compositions useful for removing nail lacquer from the nail surface, including aerosolizable compositions.

BACKGROUND

In general, nail polish (lacquer) compositions include cosmetic compositions developed for decorating, treating or protecting a subject's nails, such as a person's fingernails and/or toenails. These products are frequently designed to provide color and other visual effects to the nails of the person's hands and feet. Nail polishes typically contain organic polymers such as nitrocellulose and acrylates, thickeners, plasticizers, ultraviolet-absorbing compounds, dyes, pigments and/or glitter. Products developed for removal of nail polish from fingernails and toenails typically consist of a volatile solvent which may dissolve the lacquer.

SUMMARY

The compositions described herein advantageously remove nail polish as desired, but result in little or no drying of the nail. In some embodiments, this can be observed even with compositions that contain acetone. The compositions can be prepared to be very stable compositions. In some embodiments, the present compositions are aerosolizable.

Generally, the aerosolizable compositions involve the implementation of a stable propellant so that the overall compositions and methods are safe and effective. An example of such a propellant is carbon dioxide ($CO_2$). Notwithstanding the foregoing, optionally any appropriate propellant can be used, such a hydrocarbon propellant. One example of a hydrocarbon propellant is hydrofluorocarbon 152A. An example of a hydrocarbon propellant is propane. Additional exemplary hydrocarbon propellants include butane, butane/propane blends, isobutane for hydrocarbon. An example of a hydrofluorocarbon propellant example is 152A. Additional examples of hydrofluorocarbon propellants include HFC 134A, difluoromethane, pentafluoroethane and pentafluoropropane. Further examples, which are considered environmentally oriented, include trans-dichloroethylene, bromoethane and bromopropane. Examples of hydroflurooleofin propellants include HFO1234ZE, HFO1234ZD and HFO1234YZ.

The aerosolizable compositions may be stored in various aerosol containers. In general, the materials from which the aerosol container is made are selected so that the compositions have little or no detrimental impact on the container. For example, in some embodiments, the container is formed of a material that is not soluble in the composition. Optionally, the aerosol container is not formed of a plastic. However, in certain embodiments, an appropriate (resistant) plastic can be used for the aerosol container. Such plastics include, for example, HDPE, PTFE, HDPP and the like. In some embodiments, the aerosol container is made of a metal-containing material, such as stainless steel or aluminum. In certain embodiments, the aerosol container is designed to result in little or no acetone evaporation from the composition when housed within the container. In some embodiments, the container and the composition are selected to attain a desired coarseness of the aerosol, e.g., so that the aerosol appropriately wets a cotton ball in five seconds or less. Typically, the composition is disposed in the aerosol container, and then the container is pressurized. Often, the pressure is at least about 40 pounds per square inch (p.s.i.), and at most about 140 p.s.i., although a pressure outside this range may be used if appropriate. In some embodiments, the pressure inside the container is about 40-110 p.s.i., e.g., about 80-110 p.s.i.

Optionally, the composition contains one or more additional components that assist in proper maintenance and care of the nail. Examples include, but are not limited to, a component that strengthens or hardens nails, a component that moisturizes skin and nails, a component that hydrates cuticles, and a component that lowers loss of moisture from the skin.

Implementations of the present disclosure may include one or more of the following features.

In one general aspect, the disclosure provides a solvent composition that includes: i) a volatile at least partially water-miscible aprotic organic solvent in an amount from about 65 w/w % to about 85 w/w %; ii) a non-volatile water-immiscible aprotic organic solvent in an amount from about 8 w/w % to about 20 w/w %; and iii) a non-volatile at least partially water-miscible aprotic organic solvent in an amount from about 8 w/w % to about 20 w/w %.

In another general aspect, the disclosure provides a solvent composition that includes: i) a volatile water-miscible aprotic organic solvent in an amount from about 10 w/w % to about 50 w/w %; and ii) a non-volatile water-immiscible aprotic organic solvent in an amount from about 50 w/w % to about 90 w/w %.

In a further general aspect, the disclosure provides a method that includes removing polish from a nail using a solvent composition disclosed herein.

In yet another general aspect, the disclosure provides an aerosolizable composition that includes: i) a non-volatile water-immiscible aprotic organic solvent; ii) a non-volatile at least partially water-miscible aprotic organic solvent; and iii) a propellant.

In still another general aspect, the disclosure provides an aerosolizable composition that includes: i) a volatile water-miscible aprotic organic solvent other than acetone; and ii) a propellant.

In one general aspect, the disclosure provides an aerosolizable composition that includes: i) a non-volatile water-immiscible aprotic organic solvent; ii) a propellant; and iii) at least one additional ingredient, wherein the additional ingredient is selected from: an ingredient that strengthens or hardens nails, an ingredient that moisturizes skin and nails, an ingredient that hydrates cuticles, and an ingredient that lowers loss of moisture from the skin.

In a further general aspect, the disclosure provides an aerosol container that includes: i) a vessel (e.g., metallic vessel, appropriate plastic vessel); and ii) a valve mounted on top of the vessel, wherein the vessel also includes an aerosolizable composition disclosed herein.

In another general aspect, the disclosure provides a method that includes removing polish from a nail using an aerosolizable composition disclosed herein. The method can include dispensing the aerosolizable composition from an aerosol container.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control. Other features and advantages of the present application will be apparent from the following detailed description and figures, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A is an image showing the components of an aerosol valve.

FIG. 1B is an image showing an assembled aerosol valve.

FIG. 2 is a photograph showing a nail coated with a nail lacquer.

FIG. 3 is a photograph showing a nail after the removal of nail lacquer using an acetone-containing aerosolizable composition according to an embodiment of the disclosure.

FIG. 4 is a photograph showing a nail after the removal of nail lacquer using an acetone-free aerosolizable composition according to another embodiment of the disclosure.

FIG. 5 is a photograph showing a nail after the removal of nail lacquer using regular acetone.

FIG. 6A is an image showing an aerosol container with a bag-on-valve.

FIG. 6B is an image showing a typical process of filling an aerosol container containing a bag-on-valve with a solvent composition.

DETAILED DESCRIPTION

Introduction

In general, the disclosure provides various compositions that can be cosmetic compositions. Such compositions can be used, for example, to remove nail polish from a nail.

In one general aspect, the compositions can be considered to be in two different general categories: those which contain acetone; and those which are acetone-free.

Optionally, the compositions can be aerosolizable compositions (e.g., in an aerosol container with a propellant).

Acetone-Containing Compositions

While we refer to "acetone-containing" compositions herein, it is to be understood that such compositions can contain, in addition to or instead of acetone, any volatile at least partially water-miscible aprotic organic solvent. Acetone is but one example of an at least partially water-miscible aprotic organic solvent.

In general, acetone-containing compositions contain: i) a volatile at least partially water-miscible aprotic organic solvent, e.g., acetone; ii) a non-volatile water-immiscible aprotic organic solvent, e.g., butyl acetate; and iii) a non-volatile at least partially water-miscible aprotic organic solvent, e.g., propylene carbonate. In some embodiments, these are the only ingredients in the composition. In certain embodiments, the composition can contain one or more additional ingredients, as discussed below.

As used herein, the term "water-miscible" refers to a solvent that may be mixed with water in any proportion to form a homogenous liquid. As used herein, the term "partially water-miscible" refers to a solvent characterized in that when an amount of the solvent is mixed with the equal amount of water, at least about 5 wt. % (e.g., at least about 10 wt. %, at least about 15 wt. %, at least about 20 wt. %, or at least about 30 wt. %) of the solvent is miscible with water at room temperature, while the rest of the amount of the solvent forms a separate phase/layer. For example, when 100 mg of partially water-miscible solvent is mixed with 100 mg of water, at least 5 mg (e.g., at least about 10 mg, at least about 15 mg, at least about 20 mg, at least about 30 mg) of the solvent is completely miscible with water, while the rest of the amount of the solvent is not miscible with water and forms a separate phase/layer at room temperature. As used herein, the term "water-immiscible" refers to a solvent that is incapable of being mixed with water to form a homogeneous liquid. For example, solubility of the water-immiscible solvent in water is less than about 3 wt. % (e.g., less than about 2 wt. %, or less than about 1 wt. %). For example, less than about 3 g, less than about 2 g, or less than about 1 g of water-immiscible solvent is soluble 100 mL of water.

As used herein, the term "volatile" refers to a solvent that is easily evaporated (i.e., easily vaporizes) from a container or a surface at ambient temperature. In some embodiments, 1 mL of a volatile solvent evaporates in about 1-10 min at ordinary room temperature. Volatile solvent generally has low boiling point and high vapor pressure at ambient temperature (e.g., boiling point below about 100° C. and/or vapor pressure above about 50 mm Hg at 20° C.).

As used herein, the term "non-volatile" refers to a solvent that does not evaporate from a container or a surface at ambient temperature. In some embodiments, 1 mL of a non-volatile solvent evaporates in more than about 2-3 hours at ordinary room temperature or does not evaporate at all. Non-volatile solvent generally has high boiling point and low vapor pressure at ambient temperature (e.g., boiling point above about 100° C. and/or vapor pressure below about 20 mm Hg at 20° C.).

Exemplary Volatile at Least Partially Water-Miscible Organic Solvents

In some embodiments, a volatile at least partially water-miscible aprotic organic solvent has boiling point in the range from about 20° C. to about 85° C., from about 25° C. to about 85° C., from about 30° C. to about 80° C., from about 35° C. to about 75° C., from about 40° C. to about 70° C., or from about 45° C. to about 65° C. In some embodiments, the volatile at least partially water-miscible aprotic organic solvent has vapor pressure greater than about 70 mm Hg, about 80 mmHg, about 100 mmHg, about 150 mmHg, about 200 mmHg, about 250 mmHg, about 300 mmHg at about 20° C.

In some embodiments, a volatile aprotic organic solvent is completely water-miscible (i.e., may be mixed with water in any proportion to form a homogenous liquid). In some embodiments, the volatile aprotic organic solvent is partially water-miscible (i.e., at least about 10 wt. %, at least about 15 wt. %, at least about 20 wt. %, at least about 30 wt. % of the volatile aprotic organic solvent is miscible with the equal amount of water at room temperature).

In some embodiments, a volatile at least partially water-miscible aprotic organic solvent is a di($C_{1-3}$ alkyl) ketone, such as, for example, an acetone or a butan-2-one (also known as methyl ethyl ketone or MEK). In some embodiments, the volatile water-miscible aprotic organic solvent is acetone, tetrahydrofuran (THF), 1,3-dioxolane, dimethoxyethane (monoglyme) or acetonitrile. In some embodiments, the volatile partially water-miscible aprotic organic solvent is methyl acetate or dimethoxymethane (methylal).

In some embodiments, a volatile water-miscible aprotic organic solvent is acetone having the following formula:

In some embodiments, a volatile water-miscible aprotic organic solvent is 1,3-dioxolane having the following formula:

Exemplary Non-Volatile Water-Immiscible Aprotic Organic Solvents

In some embodiments, a non-volatile water-immiscible aprotic organic solvent has boiling point in the range from about 100° C. to about 300° C., from about 110° C. to about 250° C., from about 115° C. to about 200° C., or from about 120° C. to about 175° C. In some embodiments, the non-volatile water-immiscible aprotic organic solvent has boiling point greater than about 100° C.

In some embodiments, a non-volatile water-immiscible aprotic organic solvent has vapor pressure less than about 25 mm Hg, less than about 20 mm Hg, less than about 15 mm Hg, less than about 10 mm Hg, less than about 5 mm Hg, less than about 1 mm Hg, or less than about 0.1 mm Hg at about 20° C.

In some embodiments, a non-volatile aprotic organic solvent is completely water-immiscible (i.e., incapable of being mixed with water to form a homogeneous liquid). In some embodiments, a water solubility of the non-volatile water-immiscible aprotic organic solvent is less than about 3 g (e.g., less than about 2 g, less than about 1 g, less than about 0.8 g, or less than about 0.5 g) per 100 mL of water at 20° C.

In some embodiments, the non-volatile water-immiscible aprotic organic solvent is a $C_{1-5}$ alkyl acetate, such as methyl acetate or ethyl acetate. In some embodiments, the non-volatile water-immiscible aprotic organic solvent is a $C_{3-5}$ alkyl acetate. For example, an $C_{3-5}$ alkyl acetate is propyl acetate, n-butyl acetate, isobutyl acetate, tert-butyl acetate, sec-butyl acetate, n-amyl acetate, isoamyl acetate, tert-amyl acetate or sec-amyl acetate. In some embodiments, the non-volatile water-immiscible aprotic organic solvent is n-butyl acetate, toluene or xylene.

In some embodiments, the non-volatile water-immiscible aprotic organic solvent is n-butyl acetate having the following formula:

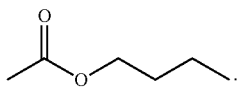

Exemplary Non-Volatile at Least Partially Water-Miscible Aprotic Organic Solvents In some embodiments, a non-volatile at least partially water-miscible aprotic organic solvent has boiling point in the range from about 100° C. to about 350° C., from about 125° C. to about 300° C., from about 140° C. to about 275° C., or from about 150° C. to about 250° C. In some embodiments, a non-volatile water-immiscible aprotic organic solvent has boiling point greater than about 150° C.

In some embodiments, a non-volatile at least partially water-miscible aprotic organic solvent has vapor pressure less than about 10 mm Hg, less than about 5 mm Hg, less than about 1 mm Hg, or less than about 0.1 mm Hg at about 20° C.

In some embodiments, a non-volatile aprotic organic solvent is completely water-miscible (i.e., may be mixed with water in any proportion to form a homogenous liquid). In some embodiments, a non-volatile aprotic organic solvent is partially water-miscible (i.e., at least 5 wt. %, at least 10 wt. %, 15 wt. %, 20 wt. % or 30 wt. % of the non-volatile aprotic organic solvent is miscible with water when equal amounts of the solvent and water are mixed at room temperature).

In some embodiments, a non-volatile at least partially water-miscible aprotic organic solvent is a cyclic carbonate, such as ethylene carbonate, trimethylene carbonate or propylene carbonate. In some embodiments, a non-volatile water-miscible aprotic organic solvent is ethylene carbonate, bis(2-methoxyethyl) ether (diglyme), triethylene glycol dimethyl ether (triglyme), tetraethylene glycol dimethyl ether (tetraglyme) or 1,4-dioxane.

In some embodiments, a non-volatile partially water-miscible aprotic organic solvent is propylene carbonate having the following formula:

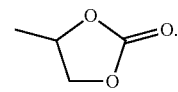

Exemplary Combinations of Solvents

In some embodiments, the amount of the volatile at least partially water-miscible aprotic organic solvent in the solvent composition is from about 20 w/w % to about 90 w/w %, from about 25 w/w % to about 90 w/w %, from about 30 w/w % to about 90 w/w %, from about 35 w/w % to about 90 w/w %, from about 40 w/w % to about 90 w/w %, from about 45 w/w % to about 90 w/w %, from about 50 w/w % to about 90 w/w %, from about 55 w/w % to about 90 w/w %, from about 60 w/w % to about 90 w/w %, from about 65 w/w % to about 90 w/w %, from about 65 w/w % to about 85 w/w %, from about 70 w/w % to about 80 w/w %. In some embodiments, the amount of the volatile at least partially water-miscible aprotic organic solvent in the solvent composition is from about 20 v/v % to about 90 v/v %, from about 25 v/v % to about 90 v/v %, from about 30 v/v % to about 90 v/v %, from about 35 v/v % to about 90 v/v %, from about 40 v/v % to about 90 v/v %, from about 45 v/v % to about 90 v/v %, from about 50 v/v % to about 90 v/v %, from about 55 v/v % to about 90 v/v %, from about 60 v/v % to about 90 v/v %, from about 65 v/v % to about 90 v/v %, from about 70 v/v % to about 90 v/v %, or from about 75 v/v % to about 85 v/v %.

In some embodiments, the amount of the non-volatile water-immiscible aprotic organic solvent in the solvent composition is from about 1 w/w % to about 60 w/w %, from about 2 w/w % to about 50 w/w %, from about 3 w/w % to about 40 w/w %, from about 4 w/w % to about 30 w/w %, from about 5 w/w % to about 25 w/w %, from about 6 w/w % to about 20 w/w %, from about 7 w/w % to about 20 w/w %, from about 8 w/w % to about 20 w/w %, from about 8 w/w % to about 18 w/w %, or from about 10 w/w % to about 15 w/w %. In some embodiments, the amount of the non-volatile water-immiscible aprotic organic solvent in the solvent composition is from about 1 v/v % to about 60 v/v %, from about 2 v/v % to about 50 v/v %, from about 3 v/v % to about 40 v/v %, from about 4 v/v % to about 30 v/v %, from about 5 v/v % to about 25 v/v %, from about 8 v/v % to about 20 v/v %, from about 8 v/v % to about 18 v/v %, or from about 10 v/v % to about 15 v/v %.

In some embodiments, the amount of non-volatile at least partially water-miscible aprotic organic solvent in the solvent composition is from about 1 w/w % to about 60 w/w %, from about 2 w/w % to about 50 w/w %, from about 3 w/w % to about 40 w/w %, from about 4 w/w % to about 30 w/w %, from about 5 w/w % to about 25 w/w %, from about 6 w/w % to about 20 w/w %, from about 7 w/w % to about 20 w/w %, from about 8 w/w % to about 20 w/w %, from about 8 w/w % to about 18 w/w %, or from about 10 w/w % to about 15 w/w %. In some embodiments, the amount of the non-volatile at least partially water-miscible aprotic organic solvent in the solvent composition is from about 1 v/v % to about 50 v/v %, from about 2 v/v % to about 40 v/v %, from about 3 v/v % to about 30 v/v %, from about 3 v/v % to about 25 v/v %, from about 3 v/v % to about 20 v/v %, from about 4 v/v % to about 20 v/v %, from about 4 v/v % to about 18 v/v %, from about 5 v/v % to about 15 v/v %, or from about 6 v/v % to about 12 v/v %.

In some embodiments, the solvent composition contains equal amounts (e.g., by weight or by volume) of the non-volatile water-immiscible aprotic organic solvent and the non-volatile at least partially water-miscible aprotic organic solvent.

In some embodiments, the solvent composition contains at least (i) a volatile at least partially water-miscible organic solvent in an amount from about 65 w/w % to about 85 w/w %; (ii) a non-volatile water-immiscible aprotic organic solvent in an amount from about 8 w/w % to about 20 w/w %; and (iii) a non-volatile at least partially water-miscible aprotic organic solvent in an amount from about 8 w/w % to about 20 w/w %.

In some embodiments, the solvent composition contains at least (i) a volatile at least partially water-miscible organic solvent in an amount from about 70 w/w % to about 80 w/w %; (ii) a non-volatile water-immiscible aprotic organic solvent in an amount from about 10 w/w % to about 15 w/w %; and (iii) a non-volatile at least partially water-miscible aprotic organic solvent in an amount from about 10 w/w % to about 15 w/w %.

In some embodiments, the solvent composition contains at least (i) a volatile at least partially water-miscible organic solvent in an amount from about 70 v/v % to about 90 v/v %; (ii) a non-volatile water-immiscible aprotic organic solvent in an amount from about 10 v/v % to about 15 v/v %; and (iii) a non-volatile at least partially water-miscible aprotic organic solvent in an amount from about 6 v/v % to about 12 v/v %.

In some embodiments, the solvent composition contains at least acetone; butyl acetate; and propylene carbonate. In such embodiments, the relative amounts of the ingredients can vary. As an example, the composition contains equal amounts (by weight or by volume) of butyl acetate and propylene carbonate. As another example, the solvent composition can contain acetone in an amount from about 70 w/w % to about 80 w/w % (or from about 75 v/v % to about 85 v/v %); and the rest is butyl acetate and propylene carbonate in equal amounts (by weight or by volume). As a further example, the solvent composition can contain butyl acetate in an amount from about 10 w/w % to about 15 w/w % (or from about 10 v/v % to about 15 v/v %); and the rest is propylene carbonate and acetone. As an additional example, the solvent composition can contain propylene carbonate in an amount from about 10 w/w % to about 15 w/w % (or from about 5 v/v % to about 15 v/v %); and the rest is butyl acetate and acetone. In some embodiments, the acetone-containing composition does not contain an estasol dibasic ester solvent (e.g., dimethyl butanedioate; dimethyl hexanedioate; dimethyl pentanedioate, or a mixture thereof).

In some embodiments, the solvent composition contains at least: (i) acetone in an amount from about 70 w/w % to about 80 w/w %; (ii) butyl acetate in an amount from about 10 w/w % to about 15 w/w %; and (iii) propylene carbonate in an amount from about 10 w/w % to about 15 w/w %.

In some embodiments, the solvent composition contains at least: (i) acetone in an amount from about 75 v/v % to about 85 v/v %; (ii) butyl acetate in an amount from about 10 v/v % to about 20 v/v %; and (iii) propylene carbonate in an amount from about 6 v/v % to about 12 v/v %.

In some embodiments, the acetone-containing solvent composition is a cosmetic composition. For example, the acetone-containing solvent composition is a nail polish remover composition.

In some embodiments, the acetone-containing solvent composition is substantially anhydrous. As used herein, "substantially anhydrous" refers to a composition that contains at most 1 wt. % water. In some embodiments, the acetone-containing solvent composition contains at most 3 wt. % water, at most 2 wt. % water, at most 1 wt. % water, at most 0.5 wt. % water, or at most 0.1 wt. % water.

Exemplary Physical Properties

In some embodiments, the evaporation rate of the solvent composition is lower than the evaporation rate of pure acetone. Such evaporation rates can allow the composition to be used to remove nail polish from a nail using a method in which the composition is first used to wet an absorbent material, followed by contacting the wetted absorbent material with the nail polish. If the evaporation rate were too high, it may be difficult to effectively wet the absorbent material. If the evaporation rate were too low, it may be difficult to have one or more of the solvents in the composition evaporate at the appropriate time in the process of removing the nail polish.

In some embodiments, the viscosity of the solvent composition is less than 1000 cP, less than 1 cP, less than 0.9 cP, less than 0.8 cP, less than 0.7 cP, less than 0.6 cP, or less than 0.5 cP. Such viscosities can allow the composition to be used to remove nail polish from a nail using a method in which the composition is aerosolized and first used to wet an absorbent material, followed by contacting the wetted absorbent material with the nail polish. If the viscosity of the composition were too high, it may be difficult to aerosolize the composition.

In some embodiments, the flash point of the solvent composition is lower than the flash point of pure acetone. Such flash points can allow the composition to be used to remove nail polish from a nail while having relatively low flammability.

In some embodiments, the density of the composition is from about 0.4 g/mL to about 1.2 g/mL, from about 0.6 g/mL to about 1.0 g/mL, or about 0.7 g/mL to about 0.9 g/mL. In some embodiments, the density of the composition is about 0.8 g/mL. Such densities can allow the composition to be used to remove nail polish from a nail using a method in which the composition is aerosolized and first used to wet an absorbent material, followed by contacting the wetted absorbent material with the nail polish. If the density of the composition were too high, it may be difficult to aerosolize the composition.

In some embodiments, the Kauri butanol value of the composition is greater than 1, greater than 50, greater than 100, greater than 150, greater than 250 or greater than 300. Such Kauri butanol values can allow for good solvency of the composition.

Exemplary Preparation Methods

In some embodiments, the solvent composition may be prepared by mixing the volatile at least partially water-miscible aprotic organic solvent (e.g., acetone), the non-volatile water-immiscible aprotic organic solvent (e.g., butyl acetate) and the non-volatile at least partially water-miscible aprotic organic solvent (e.g., propylene carbonate) in a reaction vessel such as a beaker or an Erlenmeyer flask. The mixing may be conducted with agitation or stirring, for example by using a rod, a mechanical stirrer or a magnetic stirrer. In some embodiments, the mixing is carried out at ambient temperature (e.g., room temperature) or at lower temperature, for example at about 0° C., about 5° C. (e.g., about 10° C., at about 15° C.). In some embodiments, the mixing is conducted from 10 seconds to 1 hour (e.g., from 20 seconds to 45 min, from 30 seconds to 15 min, from 30 seconds to 5 min, or from 30 seconds to 1 min). In some embodiments, the mixing is conducted until formation of a clear homogenous liquid is visually observed.

Exemplary Optional Additional Ingredients

In some embodiments, when the solvent composition is a nail polish remover composition, the composition further includes at least one additional ingredient, wherein the additional ingredient is selected from: an ingredient that strengthens or hardens nails (e.g., keratin amino acids, collagen, or ceramides such as ceramide NP); an ingredient that moisturizes skin and nails (e.g., oleyl lactate, $C_6$-$C_{22}$ lactates, and coconut oil and/or other vegetable oils suitable for skin and nail use); an ingredient that hydrates cuticles (e.g., sodium hyaluronate); and an ingredient that lowers loss of moisture from the skin (e.g., cocoa butter, shea butter, other shea extracts). Optionally, a solvent composition can contain each of these additional ingredients. In some embodiments, the solvent composition contains a humectant (e.g., propylene glycol).

In some embodiments, the ingredient that moisturizes skin and nails contains a $C_6$-$C_{30}$ alkyl lactate, or a mixture thereof. As used herein, the term "$C_6$-$C_{30}$ alkyl" refers to a saturated or partially unsaturated hydrocarbon group that may be straight-chain, branched or cyclic, having 6 to 30 carbon atoms. In some embodiments, an unsaturated $C_6$-$C_{30}$ alkyl contains 1, 2, 3, 4, 5, or 6 double bonds. Suitable examples of unsaturated $C_6$-$C_{30}$ alkyl groups include oleyl ($C_{18}H_{35}$), linoleyl ($C_{18}H_{33}$), linolenyl ($C_{18}H_{31}$), eicosapentaenyl ($C_{20}H_{31}$), and docosahexaenyl ($C_{22}H_{33}$). In some embodiments, the $C_6$-$C_{30}$ alkyl is a straight chain saturated alkyl. Suitable examples of such saturated $C_6$-$C_{30}$ alkyls include any alkyl group between $C_8H_{17}$ (octyl) and $C_{30}H_{61}$ (triacontyl), such as decyl ($C_{10}H_{21}$), myristyl ($C_{14}H_{29}$), behenyl ($C_{22}H_{45}$), lauryl ($C_{12}H_{25}$) and stearyl ($C_{18}H_{37}$).

In some embodiments, the ingredient that moisturizes skin and nails contains one or more of $C_6$-$C_{30}$ alkyl lactates selected from: oleyl lactate, linoleyl lactate, linolenyl lactate, decyl lactate, behenyl lactate, myristyl lactate, lauryl lactate, stearyl lactate, an ester of lactic acid and EPA alcohol (eicosapentaenyl alcohol), and an ester of lactic acid and DHA alcohol (docosahexaenyl alcohol).

In some embodiments, the ingredient that moisturizes skin and nails contains a mixture of oleyl lactate and at least one of $C_6$-$C_{30}$ alkyl lactates selected from: linoleyl lactate, linolenyl lactate, decyl lactate, behenyl lactate, myristyl lactate, lauryl lactate, stearyl lactate, an ester of lactic acid and EPA alcohol (eicosapentaenyl alcohol), and an ester of lactic acid and DHA alcohol (docosahexaenyl alcohol).

In some embodiments, the amount of $C_6$-$C_{30}$ alkyl lactates in the nail polish remover composition is from about 0.5 w/w % to about 5 w/w %, from about 0.5 w/w % to about 3 w/w %, from about 1 w/w % to about 3 w/w %, from about 1 w/w % to about 2 w/w %, about 0.5 w/w %, about 1 w/w %, about 1.5 w/w %, about 2 w/w %, about 3 w/w % or about 4 w/w %.

In some embodiments, the ingredient that moisturizes skin and nails contains a coconut oil. In such embodiments, the amount of the coconut oil in the nail polish remover composition is from about 0.1 w/w % to about 3 w/w %, from about 0.15 w/w % to about 2.5 w/w %, from about 0.2 w/w % to about 2 w/w %, from about 0.3 w/w % to about 2 w/w %, %, from about 0.3 w/w % to about 1 w/w %, about 0.1 w/w %, about 0.2 w/w %, about 0.3 w/w %, about 0.5 w/w %, about 0.75 w/w %, about 1 w/w % or about 2 w/w %.

In some embodiments, the ingredient that moisturizes skin and nails contains one or more of the $C_6$-$C_{30}$ alkyl lactates and the coconut oil. In such embodiments, the combined amount of the of the $C_6$-$C_{30}$ alkyl lactates and the coconut oil in the nail polish remover composition is from about 1 w/w % to about 3 w/w %.

Application of a moisturizing ingredient to skin typically leaves a thin greasy film on the person's skin. Such a greasy film is associated with the moisturizing effect of the ingredient, but may be considered unpleasant and undesirable by many. In some embodiments, the ingredient that moisturizes skin and nails is present in the nail polish remover composition in an amount that advantageously avoids undesirable nail whitening after the nail polish remover composition is applied to remove the polish from the nail, and yet does not form a greasy film on a person's skin and nails.

In some embodiments, the nail polish remover solvent composition includes an ingredient that moisturizes skin and nails, an ingredient that strengthens or hardens nails, and an ingredient that lowers loss of moisture from the skin. In such embodiments, the combined amount of the ingredient that strengthens or hardens nails and the ingredient that lowers loss of moisture from the skin can be from about 0.5 w/w % to about 5 w/w %, from about 0.5 w/w % to about 4 w/w %, from about 0.5 w/w % to about 3 w/w %, from about 0.5 w/w % to about 1.5 w/w %, about 0.5 w/w %, equal to or less than about 1 w/w %, about 1.5 w/w %, about 2 w/w %, about 4 w/w % or about 5 w/w %. Further in such embodiments, the amount of the ingredient that moisturizes skin and nails can be from about 0.5 w/w % to about 5 w/w %, from about 0.5 w/w % to about 4 w/w %, from about 0.5 w/w % to about 3 w/w %, from about 0.5 w/w % to about 1.5 w/w %, about 0.5 w/w %, equal to or greater than about 1 w/w %, about 1.5 w/w %, or about 2 w/w %. Yet further in such embodiments, the composition includes oleyl lactate in an amount of less than about 0.5 w/w %, equal to or greater than about 1 w/w %, about 1.5 w/w %, about 2 w/w %, or from about 1 w/w % to about 2 w/w %, from about 1 w/w % to about 3 w/w %, or from about 1 w/w % to about 5 w/w %; and keratin amino acids and cocoa butter in the combined amount equal to or less than about 1 w/w %, about 1.5 w/w %, about 2 w/w %, about 3 w/w %, about 4 w/w %, or about 5 w/w %, or from about 0.5 w/w % to about 5 w/w %.

In some embodiments, the nail polish remover solvent composition includes an ingredient that moisturizes skin and nails, an ingredient that strengthens or hardens nails, and an ingredient that hydrates cuticles. In such embodiments, the combined amount of the ingredient that strengthens or hardens nails and the ingredient that hydrates cuticles can be from about 0.5 w/w % to about 5 w/w %, from about 0.5 w/w % to about 4 w/w %, from about 0.5 w/w % to about 3 w/w %, from about 0.5 w/w % to about 1.5 w/w %, about 0.5 w/w %, equal to or less than about 1 w/w %, about 1.5 w/w %, about 2 w/w %, about 4 w/w % or about 5 w/w %. Further in such embodiments, the amount of the ingredient that moisturizes skin and nails can be from about 0.5 w/w % to about 5 w/w %, from about 0.5 w/w % to about 4 w/w %, from about 0.5 w/w % to about 3 w/w %, from about 0.5 w/w % to about 1.5 w/w %, about 0.5 w/w %, equal to or greater than about 1 w/w %, about 1.5 w/w %, or about 2 w/w %. Yet further in such embodiments, the composition includes oleyl lactate in an amount of less than about 0.5 w/w %, equal to or greater than about 1 w/w %, about 1.5 w/w %, about 2 w/w %, or from about 1 w/w % to about 2 w/w %; and sodium hyaluronate and collagen in a combined amount equal to or less than about 1 w/w %, about 1.5 w/w %, about 2 w/w %, about 3 w/w %, about 4 w/w %, or about 5 w/w %.

In some embodiments, enhanced ability to avoid undesirable nail whitening can be achieved by adding a humectant to the nail polish remover solvent composition. In such embodiments, when the solvent composition is applied to remove the polish from the nail, the humectant promotes the precipitation of the moisturizing ingredient from the solvent composition and facilitates application of the moisturizing ingredient to the skin and nails. In some embodiments, the humectant is absorbed by the skin and helps the skin to retain moisture. In certain embodiments, the humectant promotes penetration of the skin by active ingredients of the nail polish remover composition (e.g., moisturizing ingredient, hydrating ingredient, ingredient that lowers loss of moisture). In some embodiments, the humectant facilities absorption of moisture and water-based ingredients by the skin. The humectant also improves skin smoothness, softness and moisture content, and provides cooling effect to the person's skin and nails. In some embodiments, the humectant draws water from the air into the skin's outer layer. In other embodiments, the humectant forms a protective layer on the person's skin that help prevent the loss of moisture form the skin. In some embodiments, the amount of humectant in the nail polish remover solvent composition is from about 0.5 w/w % to about 5 w/w %, from about 0.5 w/w % to about 3 w/w %, from about 1 w/w % to about 3 w/w %, from about 1 w/w % to about 2 w/w %, about 0.5 w/w %, about 1 w/w %, about 1.5 w/w %, about 2 w/w %, about 3 w/w % or about 4 w/w %. In some embodiments, the humectant is selected from: propylene glycol, hexylene glycol, butylene glycol, glycerin, glyceryl triacetate, polymeric polyols such as polydextrose, and sugar alcohols such as sorbitol, xylitol and maltitol, and a combination thereof. In some embodiments, the humectant is propylene glycol. In such embodiments, the amount of propylene glycol in the nail polish solvent composition is from about 1 w/w % to about 3 w/w %, about 1 w/w %, about 1.5 w/w %, about 2 w/w %, about 2.5 w/w %, or about 3 w/w %. In other embodiments, the humectant is glycerin. In yet other embodiments, the humectant is a mixture of propylene glycol and glycerin.

Acetone-Free Solvent Compositions

While we refer to "acetone-free" compositions herein, it is to be understood that such compositions can contain a small amount of acetone (e.g., less than about 1 wt. % of acetone).

In general, acetone-free solvent compositions contain: i) a volatile water-miscible aprotic organic solvent other than acetone, e.g., 1,3-dioxalane; and ii) a non-volatile water-immiscible aprotic organic solvent, e.g., butyl acetate. In some embodiments, these are the only ingredients in the composition. In certain embodiments, the composition can contain one or more additional ingredients, as discussed herein.

Volatile Water-Miscible Aprotic Organic Solvent Other than Acetone

Examples of volatile water-miscible aprotic organic solvents other than acetone include those described above in the "Exemplary volatile at least partially water-miscible organic solvents" section of the "Acetone-containing solvent compositions" section. It is to be noted that in acetone-free compositions, the volatile water-miscible aprotic organic solvent is not acetone. In some embodiments, the volatile water-miscible aprotic organic solvent is 1,3-dioxolane.

Non-Volatile Water-Immiscible Aprotic Organic Solvent

Examples of non-volatile water-immiscible aprotic organic solvents include those described above in the "Exemplary non-volatile water-immiscible aprotic organic solvents" section of the "Acetone-containing solvent compositions" section. In some embodiments, the non-volatile water-immiscible aprotic organic solvent is n-butyl acetate.

Exemplary Combinations of Solvents

In some embodiments, the amount of the volatile water-miscible aprotic organic solvent in the acetone-free solvent composition is from about 1 w/w % to about 75 w/w %, from about 2 w/w % to about 70 w/w %, from about 3 w/w % to about 70 w/w %, from about 5 w/w % to about 70 w/w %, from about 7 w/w % to about 65 w/w %, from about 8 w/w % to about 60 w/w %, from about 10 w/w % to about 50 w/w %, from about 10 w/w % to about 40 w/w %, from about 15 w/w % to about 35 w/w %, from about 20 w/w % to about 30 w/w %, from about 25 w/w % to about 50 w/w %, or from about 35 w/w % to about 45 w/w %. In some embodiments, the amount of the volatile water-miscible aprotic organic solvent in the acetone-free solvent composition is about 25 w/w %. In some embodiments, the amount of the volatile water-miscible aprotic organic solvent in the acetone-free solvent composition is from about 10 v/v % to about 75 v/v %, from about 12 v/v % to about 70 v/v %, from about 15 v/v % to about 60 v/v %, from about 15 v/v % to about 50 v/v %, from about 20 v/v % to about 50 v/v %, from about 15 v/v % to about 35 v/v %, or from about 22 v/v % to about 45 v/v %. In some embodiments, the amount of the volatile water-miscible aprotic organic solvent in the acetone-free solvent composition is about 22 v/v %.

In some embodiments, the amount of the non-volatile water-immiscible aprotic organic solvent in the acetone-free solvent composition is from about 20 w/w % to about 90 w/w %, from about 25 w/w % to about 90 w/w %, from about 30 w/w % to about 90 w/w %, from about 35 w/w % to about 90 w/w %, from about 40 w/w % to about 90 w/w %, from about 45 w/w % to about 90 w/w %, from about 50 w/w % to about 90 w/w %, from about 50 w/w % to about 75 w/w %, from about 55 w/w % to about 90 w/w %, from about 60 w/w % to about 90 w/w %, from about 65 w/w % to about 90 w/w %, from about 65 w/w % to about 85 w/w %, from about 70 w/w % to about 80 w/w %. In some embodiments, the amount of the non-volatile water-immiscible aprotic organic solvent in the acetone-free solvent composition is about 75 w/w %. In some embodiments, the amount of the volatile at least partially water-miscible aprotic organic solvent in the solvent composition is from about 20 v/v % to about 90 v/v %, from about 25 v/v % to about 90 v/v %, from about 30 v/v % to about 90 v/v %, from about 35 v/v % to about 90 v/v %, from about 40 v/v % to about 90 v/v %, from about 45 v/v % to about 90 v/v %, from about 50 v/v % to about 90 v/v %, from about 55 v/v % to about 90 v/v %, from about 55 v/v % to about 80 v/v %, from about 60 v/v % to about 90 v/v %, from about 65 v/v % to about 90 v/v %, from about 70 v/v % to about 90 v/v %, or from about 75 v/v % to about 85 v/v %. In some embodiments, the amount of the volatile at least partially water-miscible aprotic organic solvent in the solvent composition is about 78 v/v %.

In some embodiments, the acetone-free solvent composition contains at least (i) a volatile water-miscible aprotic organic solvent in an amount from about 15 w/w % to about 35 w/w %; and (ii) a non-volatile water-immiscible aprotic organic solvent in an amount from about 65 w/w % to about 85 w/w.

In some embodiments, the acetone-free solvent composition contains at least (i) a volatile water-miscible aprotic organic solvent in an amount from about 20 w/w % to about 30 w/w %; and (ii) a non-volatile water-immiscible aprotic organic solvent in an amount from about 10 w/w % to about 80 w/w.

In some embodiments, the solvent composition contains at least (i) a volatile water-miscible organic solvent in an amount from about 15 v/v % to about 35 v/v %; and (ii) a non-volatile water-immiscible aprotic organic solvent in an amount from about 70 v/v % to about 90 v/v %.

In some embodiments, the acetone-free solvent composition contains at least 1,3-dioxolane and butyl acetate. In some embodiments, the acetone-free solvent composition contains 1,3-dioxolane in an amount from about 15 w/w % to about 35 w/w % (or from about 15 v/v % to about 35 v/v %); and the rest is butyl acetate. In some embodiments, the acetone-free solvent composition contains butyl acetate in an amount from about 60 w/w % to about 90 w/w % (or from about 65 v/v % to about 95 v/v %); and the rest is 1,3-dioxolane.

In some embodiments, the acetone-free solvent composition contains at least: 1,3-dioxolane in an amount from about 15 w/w % to about 35 w/w %; and butyl acetate in an amount from about 65 w/w % to about 85 w/w %.

In some embodiments, the acetone-free solvent composition contains at least: 1,3-dioxolane in an amount from about 20 w/w % to about 30 w/w %; and butyl acetate in an amount from about 70 w/w % to about 80 w/w %.

In some embodiments, the acetone-free solvent composition contains at least: 1,3-dioxolane in an amount from about 15 v/v % to about 35 v/v %; and butyl acetate in an amount from about 65 v/v % to about 85 v/v %.

In some embodiments, the acetone-free solvent composition is a cosmetic composition. For example, the acetone-free solvent composition is a nail polish remover composition.

In some embodiments, the acetone-free solvent composition is substantially anhydrous. In some embodiments, the acetone-containing solvent composition contains at most 3 wt. % water, at most 2 wt. % water, at most 1 wt. % water, at most 0.5 wt. % water, or at most 0.1 wt. % water.

In some embodiments, the acetone-free solvent composition further includes water. In some embodiments, the amount of water in the acetone-free solvent composition is about 1 w/w %, about 1.5 w/w %, about 2 w/w %, about 3 w/w %, about 5 w/w % or greater.

Exemplary Physical Properties

In some embodiments, the evaporation rate of the acetone-free solvent composition is lower than the evaporation rate of pure acetone. Such evaporation rates can allow the composition to be used to remove nail polish from a nail using a method in which the composition is first used to wet an absorbent material, followed by contacting the wetted absorbent material with the nail polish. If the evaporation rate were too high, it may be difficult to effectively wet the absorbent material. If the evaporation rate were too low, it may be difficult to have one or more of the solvents in the composition evaporate at the appropriate time in the process of removing the nail polish.

In some embodiments, the viscosity of the acetone-free solvent composition is less than 1000 cP, less than 1 cP, less than 0.9 cP, less than 0.8 cP, less than 0.7 cP, less than 0.6 cP, or less than 0.5 cP. Such viscosities can allow the composition to be used to remove nail polish from a nail using a method in which the composition is aerosolized and first used to wet an absorbent material, followed by contacting the wetted absorbent material with the nail polish. If the viscosity of the composition were too high, it may be difficult to aerosolize the composition.

In some embodiments, the flash point of the solvent composition is lower than the flash point of pure acetone. Such flash points can allow the composition to be used to remove nail polish from a nail while having relatively low flammability.

In some embodiments, the density of the composition is from about 0.4 g/mL to about 1.2 g/mL, from about 0.6 g/mL to about 1.2 g/mL, or about 0.7 g/mL to about 1.1 g/mL. Such densities can allow the composition to be used to remove nail polish from a nail using a method in which the composition is aerosolized and first used to wet an absorbent material, followed by contacting the wetted absorbent material with the nail polish. If the density of the composition were too high, it may be difficult to aerosolize the composition.

In some embodiments, the Kauri butanol value of the composition is greater than 1, greater than 50, greater than 100, greater than 150, greater than 250 or greater than 300. Such Kauri butanol values can allow for good solvency of the composition.

Exemplary Preparation Methods

In some embodiments, the acetone-free solvent composition may be prepared by mixing the volatile water-miscible aprotic organic solvent (e.g., 1,3-dioxolane) and the non-volatile water-immiscible aprotic organic solvent (e.g., butyl acetate) in a reaction vessel such as a beaker or an Erlenmeyer flask. The mixing may be carried out, for example, as described above in the "Exemplary preparation methods" section of the "Acetone-containing compositions" section.

Exemplary Optional Additional Ingredients

Exemplary optional additional ingredients include those described above in the "Exemplary optional additional ingredients" section of the "Acetone-containing solvent compositions" section. In some embodiments, a acetone-free nail polish remover solvent composition can include more than one of the noted types (or specific examples) of exemplary optional additional ingredients.

In some embodiments, the acetone-free nail polish remover solvent composition includes an ingredient that moisturizes skin and nails, and an ingredient that strengthens or hardens nails. In one embodiment, the ingredient that moisturizes skin and nails is oleyl lactate or coconut oil, and the ingredient that strengthens or hardens nails is selected from keratin amino acids, collagen, and ceramides (e.g., ceramide NP). In such embodiments, the combined amount of the ingredient that moisturizes skin and nails, and the ingredient that strengthens or hardens nails can be from about 0.5 w/w % to about 5 w/w %, from about 0.5 w/w % to about 4 w/w %, from about 0.5 w/w % to about 3 w/w %, from about 0.5 w/w % to about 1.5 w/w %, about 0.5 w/w %, less than about 1 w/w %, less than about 1.5 w/w %, less than about 2 w/w %, less than about 4 w/w % or less than about 5 w/w %. Further in such embodiments, the composition includes ceramides (e.g., ceramide NP) and coconut oil in a combined amount of less than about 1 w/w %, less than about 1.5 w/w %, less than about 2 w/w %, or less than about 3 w/w %.

Aerosolizable Compositions

As noted above, compositions disclosed herein can be aerosolizable compositions. In general, an aerosolizable composition contains a propellant.

Acetone-Containing Aerosolizable Compositions

Such compositions can contain solvents noted above in the section entitled "Acetone-containing compositions." In general, an acetone-containing aerosolizable composition also contains a propellant. For example, in some embodiments, an acetone-containing aerosolizable composition contains: (i) a volatile at least partially water-miscible aprotic organic solvent, e.g., acetone; ii) a non-volatile water-immiscible aprotic organic solvent, e.g., butyl acetate; iii) a non-volatile at least partially water-miscible aprotic organic solvent, e.g., propylene carbonate; and iv) a propellant, e.g., carbon dioxide.

In some embodiments, an acetone-containing aerosolizable composition contains: (i) a volatile at least partially water-miscible aprotic organic solvent, e.g., acetone; ii) a propellant, e.g., carbon dioxide; and iii) and at least one ingredient noted above in the section entitled "Exemplary optional additional ingredients (e.g., oleyl lactate).

Exemplary Propellants

In general, an aerosolizable composition includes a propellant. The propellant in the aerosolizable composition may be a compressed gas (e.g., nitrogen ($N_2$), air, carbon dioxide ($CO_2$) and nitrous oxide ($N_2O$)) or a liquefied gas (e.g., a hydrocarbon such as propane, isobutane or n-butane, or mixtures thereof; dimethyl ether; or hydrofluorocarbon such as 1,1-difluoroethane (HFC-152a) or 1,1,1,2-tetrafluoroethane (HFC-134a), or mixtures thereof). In some embodiments, the propellant may be a combination of a compressed gas and a liquefied gas. In some embodiments, the propellant may be a hydrocarbon blend, for example, A-46 (propene/isobutane blend), NP-46 (propane/n-butane), or NIP-46 (propane/isobutane/n-butane blend). In some embodiments, the propellant is non-flammable. In some embodiments, the propellant may suppress flammability of the aerosolizable solvent composition.

In some embodiments, the propellant is at least partially soluble in at least one solvent of the aerosolizable composition. For example, from about 1 w/w % to about 15 w/w %, from about 1 w/w % to about 10 w/w %, from about 1 w/w % to about 5 w/w %, from about 2 w/w % to about 10 w/w %, from about 2 w/w % to about 5 w/w %, or from about 2 w/w % to about 3 w/w % of the total amount of the propellant in the aerosolizable composition is soluble in at least one solvent of the aerosolizable composition (e.g., the propellant is soluble in acetone). In some embodiments, the propellant aids in producing coarse aerosol spray (e.g., such that the aerosol spray efficiently dampens an absorbent material with the solvents of the aerosolizable composition as described herein). In some embodiments, the propellant is carbon dioxide ($CO_2$).

Exemplary Combinations of Solvents and a Propellant

In some embodiments, the amount of the non-volatile water-immiscible aprotic organic solvent in the acetone-containing aerosolizable composition is from about 1 w/w % to about 60 w/w %, from about 2 w/w % to about 50 w/w %, from about 3 w/w % to about 40 w/w %, from about 4 w/w % to about 30 w/w %, from about 5 w/w % to about 25 w/w %, from about 6 w/w % to about 20 w/w %, from about 7 w/w % to about 20 w/w %, from about 8 w/w % to about 20 w/w %, from about 8 w/w % to about 18 w/w %, or from about 10 w/w % to about 15 w/w %.

In some embodiments, the amount of non-volatile at least partially water-miscible aprotic organic solvent in the acetone-containing aerosolizable composition is from about 1 w/w % to about 60 w/w %, from about 2 w/w % to about 50 w/w %, from about 3 w/w % to about 40 w/w %, from about 4 w/w % to about 30 w/w %, from about 5 w/w % to about 25 w/w %, from about 6 w/w % to about 20 w/w %, from about 7 w/w % to about 20 w/w %, from about 8 w/w % to about 20 w/w %, from about 8 w/w % to about 18 w/w %, or from about 10 w/w % to about 15 w/w %.

In some embodiments, the amount of the propellant in the acetone-containing aerosolizable composition is from about 1 w/w % to about 20 w/w %, from about 1 w/w % to about 15 w/w %, from about 1 w/w % to about 10 w/w %, from about 2 w/w % to about 9 w/w %, from about 3 w/w % to about 8 w/w %, or from about 4 w/w % to about 7 w/w %.

In some embodiments, the composition includes a volatile at least partially water-miscible aprotic organic solvent in an amount from about 20 w/w % to about 90 w/w %, from about 25 w/w % to about 90 w/w %, from about 30 w/w % to about 90 w/w %, from about 35 w/w % to about 90 w/w %, from about 40 w/w % to about 90 w/w %, from about 45 w/w % to about 90 w/w %, from about 50 w/w % to about 90 w/w %, from about 55 w/w % to about 90 w/w %, from about 60 w/w % to about 90 w/w %, from about 65 w/w % to about 90 w/w %, from about 65 w/w % to about 85 w/w %, from about 70 w/w % to about 80 w/w %.

In some embodiments, the aerosolizable composition contains equal amounts (e.g., by weight or by volume) of the non-volatile water-immiscible aprotic organic solvent and the non-volatile at least partially water-miscible aprotic organic solvent.

In some embodiments, the solvent composition contains at least: (i) a non-volatile water-immiscible aprotic organic solvent in an amount from about 8 w/w % to about 20 w/w %; (ii) a non-volatile at least partially water-miscible aprotic organic solvent in an amount from about 8 w/w % to about 20 w/w %; and (iii) a propellant in an amount from about 1 w/w % to about 10 w/w %. In such embodiments, the composition also contains (iv) a volatile at least partially water-miscible organic solvent in an amount from about 65 w/w % to about 85 w/w %.

In some embodiments, the aerosolizable composition contains at least: (i) a non-volatile water-immiscible aprotic organic solvent in an amount from about 10 w/w % to about 15 w/w %; (ii) a non-volatile at least partially water-miscible aprotic organic solvent in an amount from about 10 w/w % to about 15 w/w %; and a propellant in an amount from about 4 w/w % to about 7 w/w %. In such embodiments, the composition also contains (iv) a volatile at least partially water-miscible organic solvent in an amount from about 70 w/w % to about 80 w/w %.

In some embodiments, the aerosolizable composition contains at least acetone; butyl acetate; propylene carbonate; and carbon dioxide. In further such embodiments, the composition contains equal amounts (by weight or by volume) of butyl acetate and propylene carbonate.

In some embodiments, the aerosolizable composition contains acetone in an amount from about 70 w/w % to about 80 w/w %; and the rest is carbon dioxide; and butyl acetate and propylene carbonate in equal amounts (by weight or by volume). In some embodiments, the aerosolizable composition contains butyl acetate in an amount from about 10 w/w % to about 15 w/w %; and the rest is carbon dioxide, propylene carbonate and acetone. In some embodiments, the solvent composition contains propylene carbonate in an amount from about 10 w/w % to about 15 w/w %; and the rest is carbon dioxide, butyl acetate and acetone.

In some embodiments, the aerosolizable composition contains at least: (i) butyl acetate in an amount from about 10 w/w % to about 15 w/w %; (ii) propylene carbonate in an amount from about 10 w/w % to about 15 w/w %; and carbon dioxide in an amount from about 4 w/w % to about 7 w/w %. In such embodiments, the aerosolizable composition also contains (iv) acetone in an amount from about 70 w/w % to about 80 w/w %.

In some embodiments, the propellant (e.g., carbon dioxide) is at least partially dissolved in at least one solvent of the aerosolizable acetone-containing composition (e.g., propellant is at least partially dissolved in acetone). For example, from about 1 w/w % to about 15 w/w %, from about 1 w/w % to about 10 w/w %, from about 1 w/w % to about 5 w/w %, from about 2 w/w % to about 10 w/w %, from about 2 w/w % to about 5 w/w %, or from about 2 w/w % to about 3 w/w % of the total amount of the propellant in the aerosolizable composition is dissolved in at least one solvent of the acetone-containing aerosolizable composition.

Exemplary Additional Ingredients

In some embodiments, an aerosolizable acetone-containing composition may contain one or more of the ingredients such as those described above under the "Exemplary optional additional ingredients" section of the "Acetone-containing compositions." Such exemplary additional ingredients can be present in the amounts noted in that section.

Aerosol Containers

In some embodiments, the present disclosure provides an aerosol container including at least: (i) a vessel (e.g., a metallic vessel, an appropriate plastic vessel) and (ii) a valve mounted on top of the vessel. In some embodiments, vessel contains the aerosolizable composition as described herein. In other embodiments (e.g., when the valve is a bag-on-valve), the vessel contains a bag filled with a solvent composition as described herein. In such embodiments, the vessel also contains a pressurized gas (e.g., nitrogen or air) between the bag and walls of the vessel.

In some embodiments, the vessel is cylindrical. In some embodiments, the vessel is a straight-wall container (e.g., having a constant diameter along the entire length of the container), a necked-in aerosol can (e.g., having a rounded top), or a shaped aerosol container (e.g., having a varying diameter along the length of the container). In some embodiments, the vessel is a one-piece container (e.g., extruded or drawn) or a two-piece container (e.g., having a body and a bottom part attached to the body). In some embodiments, the vessel is a side seam (three piece) vessel. In some embodiments, the bottom of the vessel is curved. In other embodiments, the bottom of the vessel is flat. In some embodiments, when the vessel is a two-part or three-part vessel, the parts (e.g., the body and the bottom parts) are connected by flanging, soldering or welding. In some embodiments, the metallic vessel is made from aluminum. In other embodiments, the metallic vessel is made from stainless steel (e.g., 302, 316, 440, or 420 stainless steel). In other embodiments, the metallic vessel is made from tin plated steel. In some embodiments, the metallic vessel is corrosion-resistant. The materials from which the aerosol container is made are selected such that the aerosolizable compositions have little or no detrimental impact on the material of the container. In some embodiments, the metallic vessel does not contain plastic. In some embodiments, the diameter of the aerosol vessel is from about 20 mm to about 100 mm (e.g., about 40 mm, about 60-65 mm, or about 80 mm). In such embodiments, the height of the vessel is from about 100 mm to about 500 mm (e.g., about 150 mm, about 200 mm, about 250 mm, or about 300 mm). In some embodiments, the volume of the aerosol container is from about 100 mL to about 500 mL (e.g., about 150 mL, about 177 mL, about 200 mL, or about 250 mL).

In some embodiments, a valve is mounted (i.e., crimped) on top of the metallic vessel. An exemplary aerosol container valve is shown in FIGS. 1A (showing separate aerosol valve parts) and 1B (showing an assembled aerosol valve). Referring to FIGS. 1A and 1B, an aerosol valve includes a mounting cup, a stem (having the stem orifice), a stem gasket, a spring, a housing, a dip-tube, and an actuator. The actuator of the valve opens the valve and controls the spray pattern and flow. The spring ensures closing of the valve. The stem, including the stem orifice, controls the flow and the coarseness of the spray. The housing encloses the spring and the stem. Stem gasket shields the stem orifice from the liquid composition inside the aerosol container when the aerosol container is not actuated. The dip-tube draws product in to the valve and the mounting cup holds valve parts together and allows the valve to be mounted (crimped) to the metallic vessel. Generally, pressure on the actuator depresses the stem. This interrupts the sealing action of the gasket and exposes the stem orifice to the pressurized flow of the aerosolizable composition or the solvent composition as described herein.

In some embodiments, the valve is a bag-on-valve. In such embodiments, instead of a dip-tube, the valve includes a bag that is welded to the housing of the valve. In some embodiments, the bag is a foil-based packaging bag with multi-layer film laminate (e.g., manufactured by Bemis of Neenah, Wis.). An exemplary aerosol container with the bag-on-valve and the filled bag are shown in FIG. 6A. Referring to FIG. 6A, the aerosol container comprises an aerosol can (6), a valve (1), an actuator (5), a high-barrier bag (2), a solvent composition inside the bag (3) (filled bag), and a compressed propellant gas between the bag and the walls of the aerosol can (4). In the bag-on-valve system, the compressed propellant gas is s filled into the area between the bag and the can, thus keeping the solvent composition and the propellant separate at all times. When the actuator is pressed, the internal propellant pressure squeezes the bag dispensing the bag contents. With the bag-on-valve, up to 99.5 wt. % of the solvent composition may be dispensed from the aerosol can. An aerosol container with the bag-on-valve allows to pray the aerosol mixture form the container at any angle (360° actuation). In some embodiments, the mounting cup is made from aluminum or stainless steel (e.g., 302, 316, 440, or 420 stainless steel). In some embodiments, the stem gasket is made from a rubber polymer, for example neoprene rubber, nitrile runner (BUNA), viton rubber or butyl rubber (copolymer of isobutylene with isoprene). In some embodiments, the stem gasket is made from a butyl rubber.

In some embodiments, the stem has greater than 0.08" and less than 4×0.04" in orifice. In some embodiments, the stem orifice diameter is about 0.02". The housing in the valve may have a vapor tap (a hole in the side or bottom of the housing, generally from 0.005" to 0.04" in diameter). The vapor tap helps produce a drier and warmer spray and reduces the spray droplet size. In some embodiments, the housing of the valve does not have a vapor tap or has a very low vapor tap. In some embodiments, the actuator is a non-mechanical break-up actuator (non-MBU) (allowing direct flow through the actuator resulting in a stream of aerosolizable composition). In other embodiments, the actuator is a mechanical break-up actuator (MBU) (e.g., having a swirl chamber resulting in a discernable size and shape of droplets of aerosolizable composition).

The valve may be mounted (crimped) to the metallic vessel using a collet. A collet moves into the mounting cup and spreads to a specific diameter and depth. In some embodiments, the mounting cup is placed on top of the container and crimped down to a depth of about 0.2" and with a diameter if about 1".

In some embodiments, the aerosol container with the aerosolizable composition may be prepared by filling the metallic vessel with the liquid solvent composition as described herein (e.g., acetone-containing solvent composition). The aerosol container may be further filled with the propellant by any one of the following methods: 1) by pumping propellant into the container followed by crimping the valve to the vessel; 2) by vacuuming the vessel, crimping the valve to the metallic vessel and filling the container with the propellant through the valve (e.g., with the actuator being pressed down); or 3) by crimping the valve to the vessel and impact gassing the propellant to the container valve (e.g., with the actuator being pressed down). In some embodiments, the specified amount of the solvent blend is delivered to the metallic vessel, the valve is then crimped down to the specified depth and diameter, and once the container is crimped, carbon dioxide vapor is impact gassed into the container until the desired pressure is achieved. In other embodiments, when the propellant is a liquefied gas (e.g., a hydrocarbon propellant or a blend thereof), the aerosol container may be filled with the propellant by pouring the liquefied gas (a liquid at a temperature below the boiling point of the propellant) to the metallic vessel containing the solvent blend, followed by crimping the valve to the metallic vessel as described herein and warming up the container to room temperature. In some embodiments, the aerosol container containing a bag-on-valve may be filled with a solvent composition and a propellant as shown in FIG. 6B. Referring to FIG. 6B, the filling of the aerosol container includes at least the following steps: 1) placing the bag-on-valve with the empty bag inside the container; 2) filling the space between the empty bag and the inner walls of the container with the compressed propellant gas; 3) crimping and sealing the valve on the container; 4) filling the bag with the solvent composition through the valve; and 5) placing an actuator and cap on the valve. In some aspects of these embodiments, the propellant gas is selected from: nitrogen, air and carbon dioxide.

In some embodiments, the pressure in the container is from about 20 psi to about 250 psi, from about 30 psi to about 200 psi, from about 40 psi to about 140 psi, from about 50 psi to about 130 psi, from about 60 psi to about 120 psi, or from about 80 psi to about 110 psi at ambient temperature (e.g., room temperature such as about 18-27° C.). In such embodiments, the propellant pressure in the aerosol container may be about 80 psi, about 90 psi, about 100 psi, or about 110 psi.

In some embodiments, the aerosol container upon actuation produces an aerosol spray containing coarse droplets of the aerosolizable composition (e.g., the size of the coarse droplets may be from about 1 μm to about 125 μm). In some embodiments, the combination of the valve parameters and the pressure in the aerosol container allows for producing a coarse spray such that the spray may efficiently dampen an absorbent material (e.g., the aerosol appropriately wets a cotton ball in five seconds or less). Depending on the type of the particular solvent composition, propellant, scale and the desired spray coarseness, a skilled engineer would be able to select and implement appropriate valve parts, equipment and methods to successfully fill the aerosol can with the aerosolizable composition.

Methods of Use

In some embodiments, the present disclosure provides a method of removing polish from a nail using the solvent composition. As used herein, the terms "nail polish" and "nail lacquer" are used interchangeably and refer to cosmetic compositions that solidify on the surface of a person's nail and provide color and other visual effects to the nails of the person's hands and feet. Nail polishes typically contain organic polymers such as cellulose, nitrocellulose, (poly) acrylates, (poly)methacrylates, thickeners, plasticizers, ultraviolet-absorbing compounds, dyes, pigments and/or glitter. The solvent compositions and/or the aerosolizable compositions provided herein efficiently dissolve the nail polish and subsequently help remove the nail polish from the person's nails, such that the person applying the lacquer may change the color and appearance of his or her nails.

In some embodiments, the composition may be applied to the polish to remove the polish from the nail. In this process, the solvents of the composition may dissolve the polish, and the resultant solution may be wiped away using an absorbent material such as a cotton pad, a cotton ball, or a cloth.

In other embodiments, removing nail polish from the person's nail includes (i) applying the solvent composition to a surface of an absorbent material (e.g., a cotton ball) to provide a dampened surface (e.g., dampened cotton ball); and (ii) applying the dampened surface to the polish to remove the polish from the nail. In this process, the aerosolizable composition may be sprayed on the surface of the absorbent material from the aerosol container. The coarse spray allows for efficient dampening of the surface after spraying the surface for 10 seconds or less, 5 seconds or less, or for about 2 seconds. In some embodiments, quickly spraying the absorbent material can be just enough to efficiently dampen the surface of the material. The propellant such as carbon dioxide can help fill in the pores of the absorbent material and thus aids in the efficient dampening if the surface of the absorbent material. Notwithstanding the foregoing, a non-aerosolizable composition may also be used to remove the nail polish from the nail. In this case, applying the solvent composition to a surface of an absorbent material may be carried out by dipping the absorbent material into the solvent composition, or by contacting the solvent composition with the surface of the absorbent material (e.g., pouring the solvent composition onto the surface of the absorbent material). The absorbent material may be a brush, a cotton pad, a cotton ball, cottonwool, a cloth or a sponge. In some embodiments, applying the dampened surface to the polish includes wiping or rubbing the polish with the dampened surface for the amount of time sufficient to remove the polish from the nail (e.g., wiping the polish for about 2 seconds, 5 seconds, 10 seconds or about 30 seconds). In such embodiments, gently rubbing the polish with the dampened surface is just enough to remove the polish from the nail surface. In the present methods, a dampened surface includes an amount of the solvents of the composition that is sufficient to dissolve the entire amount of polish on the nail. For example, a dampened surface allows for removing at least 70 wt. %, at least 80 wt. % or at least 90 wt. %, or 100 wt. % of the polish from the nail. In some embodiments, wiping the polish with the dampened surface removes at least 90 wt. % of the polish from the nail.

Optionally, a composition described herein can be contacted directly with a nail to remove nail polish. For example, the composition can be poured onto the nail or the nail can be dipped into the composition.

In some embodiments, when the acetone-containing composition as applied to the nail polish or the surface of the absorbent material, the volatile solvent in the composition (e.g., acetone) evaporates quickly, while the non-volatile solvents (e.g., butyl acetate and propylene carbonate) remain on the dampened surface in an amount that is sufficient to dissolve the polish and remove the polish from the nail.

The compositions of the present disclosure advantageously remove the polish from the nail without leaving any white/cloudy residue on the nail and/or surrounding skin. In some embodiments, using present compositions for removing of the polish from the nail does not weaken the nail and/or does not dry the nail or the skin adjacent to the nail surface. The use of present compositions can also avoid peeling, chipping, cracking, tearing and/or breaking of skin and nails. This can be observed even with acetone-containing compositions. The present compositions also may moisturize and strengthen or harden the nail and the skin, hydrate cuticles and/or lower the loss of moisture from the skin.

Acetone-Free Aerosolizable Compositions

Such compositions can contain solvents noted above in the section entitled "Acetone-free compositions." The propellant can include any one of the propellants described above in the "Exemplary propellants" section of the "Acetone-containing aerosolizable compositions" section.

For example, in some embodiments, the acetone-free aerosolizable composition contains at least: a volatile water-miscible aprotic organic solvent other than acetone (e.g., 1,3-dioxolane) and a propellant (e.g., carbon dioxide). Optionally, the acetone-free aerosolizable composition may further contain non-volatile water-immiscible aprotic organic solvent (e.g., butyl acetate).

In certain embodiments, an acetone-free aerosolizable composition contains at least: a non-volatile water-immiscible aprotic organic solvent (e.g., butyl acetate, ethyl acetate, or mixtures thereof); a propellant (e.g., carbon dioxide); and at least one ingredient noted above in the section entitled "Exemplary optional additional ingredients (e.g., oleyl lactate).

Exemplary Combinations of Solvents and a Propellant

In some embodiments, the amount of the volatile water-miscible aprotic organic solvent other than acetone in the acetone-free aerosolizable composition is from about 1 w/w % to about 75 w/w %, from about 2 w/w % to about 70 w/w %, from about 3 w/w % to about 70 w/w %, from about 5 w/w % to about 70 w/w %, from about 7 w/w % to about 65 w/w %, from about 8 w/w % to about 60 w/w %, from about 10 w/w % to about 50 w/w %, from about 10 w/w % to about 40 w/w %, from about 15 w/w % to about 35 w/w %, from about 20 w/w % to about 30 w/w %, or from about 25 w/w % to about 50 w/w %. In some embodiments, the amount of the volatile water-miscible aprotic organic solvent other than acetone in the acetone-free aerosolizable composition is about 25 w/w %.

In some embodiments, the amount of the propellant in the acetone-free aerosolizable composition is from about 1 w/w % to about 20 w/w %, from about 1 w/w % to about 15 w/w %, %, from about 10 w/w % to about 15 w/w %, from about 1 w/w % to about 10 w/w %, from about 2 w/w % to about 9 w/w %, from about 3 w/w % to about 8 w/w %, or from about 4 w/w % to about 7 w/w %.

In some embodiments, the amount of the non-volatile water-immiscible aprotic organic solvent in the acetone-free solvent composition is from about 10 w/w % to about 90 w/w %, from about 20 w/w % to about 90 w/w %, from about 25 w/w % to about 90 w/w %, from about 30 w/w % to about 90 w/w %, from about 35 w/w % to about 90 w/w %, from about 40 w/w % to about 90 w/w %, from about 45 w/w % to about 90 w/w %, from about 50 w/w % to about 90 w/w %, from about 50 w/w % to about 75 w/w %, from about 55 w/w % to about 90 w/w %, from about 60 w/w % to about 90 w/w %, from about 65 w/w % to about 90 w/w %, from about 65 w/w % to about 85 w/w %, from about 70 w/w % to about 80 w/w %. In some embodiments, the amount of the non-volatile water-immiscible aprotic organic solvent in the acetone-free solvent composition is about 75 w/w %.

In some embodiments, the acetone-free aerosolizable composition contains at least (i) a volatile water-miscible aprotic organic solvent other than acetone in an amount from about 15 w/w % to about 35 w/w %; and (ii) a propellant in an amount from about 1 w/w % to about 10 w/w. In such embodiments, the composition further contains non-volatile water-immiscible aprotic organic solvent in an amount from about 65 w/w % to about 85 w/w %.

In some embodiments, the aerosolizable composition contains at least 1,3-dioxolane and carbon dioxide. In such embodiments, the composition further contains butyl acetate.

In some embodiments, the aerosolizable composition contains 1,3-dioxolane in an amount from about 15 w/w % to about 35 w/w %; and the rest is carbon dioxide and butyl acetate. In some embodiments, the aerosolizable composition contains butyl acetate in an amount from about 65 w/w % to about 85 w/w %; and the rest is carbon dioxide and 1,3-dioxolane. In some embodiments, the solvent composition contains carbon dioxide in an amount from about 1 w/w % to about 10 w/w %; and the rest is butyl acetate and 1,3-dioxolane.

In some embodiments, the aerosolizable composition contains at least: (i) 1,3-dioxolane in an amount from about 15 w/w % to about 35 w/w %; (ii) carbon dioxide in an amount from about 1 w/w % to about 10 w/w %. In such embodiments, the aerosolizable composition may further contain (iii) and butyl acetate in an amount from about 65 w/w % to about 85 w/w %.

In some embodiments, the aerosolizable composition contains at least: (i) 1,3-dioxolane in an amount from about 20 w/w % to about 30 w/w %; (ii) carbon dioxide in an amount from about 4 w/w % to about 7 w/w %. In such embodiments, the aerosolizable composition may further contain (iii) and butyl acetate in an amount from about 70 w/w % to about 80 w/w %.

In some embodiments, the propellant (e.g., carbon dioxide) is at least partially dissolved in at least one solvent of the aerosolizable acetone-free composition (e.g., propellant is at least partially dissolved in 1,3-dioxolane and/or in butyl acetate). For example, from about 1 w/w % to about 15 w/w %, from about 1 w/w % to about 10 w/w %, from about 1 w/w % to about 5 w/w %, from about 2 w/w % to about 10 w/w %, from about 2 w/w % to about 5 w/w %, or from about 2 w/w % to about 3 w/w % of the total amount of the propellant in the aerosolizable composition is dissolved in at least one solvent of the acetone-free aerosolizable composition.

In some embodiments, the acetone-free aerosolizable composition further contains water. For example, the amount of water is greater than about 1 w/w %, about 2 w/w %, about 3 w/w % or about 5 w/w %.

Exemplary Additional Ingredients

Exemplary additional ingredients include those noted above under the "Exemplary optional additional ingredients" section of the "Acetone-free compositions." The ingredients can be present in an amount noted in that section.

Aerosol Containers

The aerosol container can be any of the aerosol containers noted above in the "Aerosol containers" section of the "Acetone-containing aerosolizable compositions" section of the application.

Methods of Use

The methods of use can be the same as those noted above in the "Methods of use" section of the "Acetone-containing aerosolizable compositions" section of the application.

EXAMPLES

Materials and Methods

Solvents

Acetone (CAS Registry No. 67-64-1), butyl acetate (CAS Registry No. 123-86-4), 1,3-dioxolane (CAS Registry No. 646-06-0) and propylene carbonate (CAS Registry No. 108-32-7) were ACS reagent grade or higher, having a ≥99.5% purity. Carbon dioxide ($CO_2$) used to prepare aerosolizable compositions was a food grade material at >99.9% purity.

Additional Ingredients

Oleyl lactate, other lactates such as myristyl, cetyl, behenyl, or having an alcohol moiety from $C_6$-$C_{26}$, keratin amino acids, *theobroma cacao* (cocoa) seed butter, sodium hyaluronate, collagen, shea butters (e.g., from one or more plant sources), ceramides (e.g., ceramide NP), *cocos nucifera* (coconut oil) are commercially available and may be purchased from numerous commercial sources.

Aerosol Cans

6 Fl Oz (177 mL) stainless steel/aluminum aerosol containers (cans) were used for storing aerosolizable compositions. Straight-wall, necked-in and shaped aerosol containers may be used interchangeably in the described methods.

Aerosol Valves

Standard aerosol valves were used with a butyl rubber polymer stem gasket, stainless steel or aluminum mounting cup, stem having greater than 0.08" and less than 4×0.040" in orifice (orifice diameters of 0.020" were used in the present examples), and a housing having no vapor tap (very low vapor tap housings may also be used).

Example 1

Preparation of acetone-based solvent formulation

Acetone (158 g, 200 mL), butyl acetate (26 g, 29.5 mL) and polypropylene carbonate (26 g, 21.7 mL) were mixed in a 500 mL beaker. The solvent mixture was stirred for about 30 seconds until the formation of a clear and homogeneous liquid was visually observed.

Example 2

Preparation of acetone-based solvent formulation with additional ingredients

To the solvent mixture of Example 1 oleyl lactate (2 g) was added, followed by the addition of keratin amino acids (1 g) and *theobroma cacao* (cocoa) seed butter (1 g). The resultant mixture was stirred for about 30 seconds until the formation of a clear solution was visually observed.

Example 3

Preparation of acetone-based solvent formulation with additional ingredients

To the solvent mixture of Example 1 oleyl lactate (2 g) was added, followed by the addition of sodium hyaluronate (1 g) and collagen (1 g). The resultant mixture was stirred for about 30 seconds until the formation of a clear solution was visually observed.

Example 4

Preparation of acetone-free solvent formulation

Butyl acetate (176 g, 200 mL) and 1,3-dioxolane (59 g, 56 mL) were mixed in a 500 mL beaker. The solvent mixture was stirred for about 30 seconds until the formation of a clear and homogeneous liquid was visually observed.

Example 5

Preparation of acetone-free solvent formulation with additional ingredients

Ceramide NP (1.2 g) and *Cocos Nucifera* (coconut) oil (1.2 g) were added to the solvent mixture of Example 4. The resultant mixture was stirred for about 30 seconds until the formation of a clear solution was visually observed.

Example 5a

Preparation of acetone-free solvent formulation with additional ingredients

Oleyl lactate (4.7 g), propylene glycol (4.7 g, 4.5 mL) and Coconut Oil (2 g) were added to the solvent mixture of Example 4. The resultant mixture was stirred for about 30 seconds until the formation of a clear solution was visually observed.

Example 6

Preparation of aerosolizable compositions

Solvent blend from Examples 1-5a (150-180 g) was delivered into the 6 Fl Oz aerosol can. The specified valve is placed on top of the can and crimped down to a depth of 0.200"+/−0.1 and with a diameter of 1.070"+/−0.05. Once the can is crimped, $CO_2$ vapor gas was impact gassed using a piston pump into the can until the desired pressure of 80-110 psi was achieved. Cans were tare weighed to determine the amount of $CO_2$ gas in each can (8-12 g of $CO_2$ in each can).

Example 7 determination of efficiency of nail lacquer removal

A cotton ball was impregnated with either an aerosolizable composition prepared in accordance with Example 6, or with pure acetone. Spraying the cotton ball twice from the aerosol can as prepared in Example 6 was sufficient to soak the cotton ball with the solvent formulation. Nails coated with an equal amount of an opaque red nail lacquer were treated with the solvent-impregnated cotton balls.

Figure 1A:
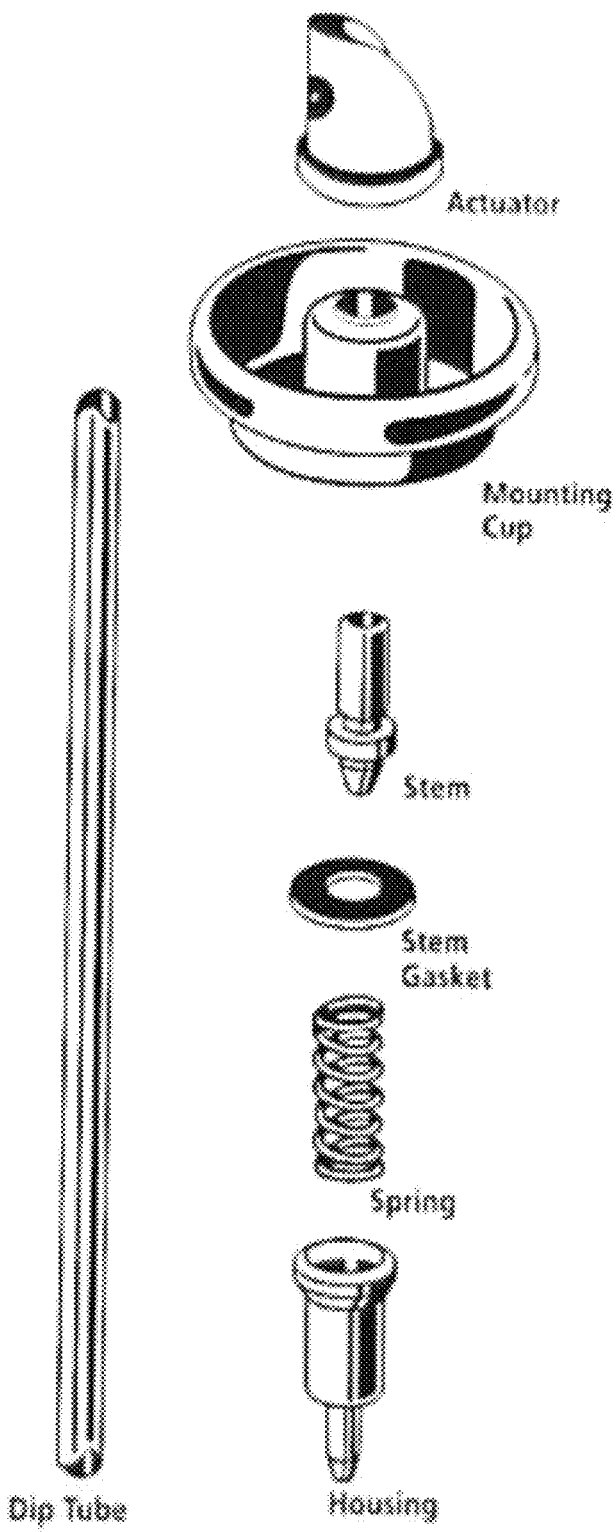
Figure 1B:
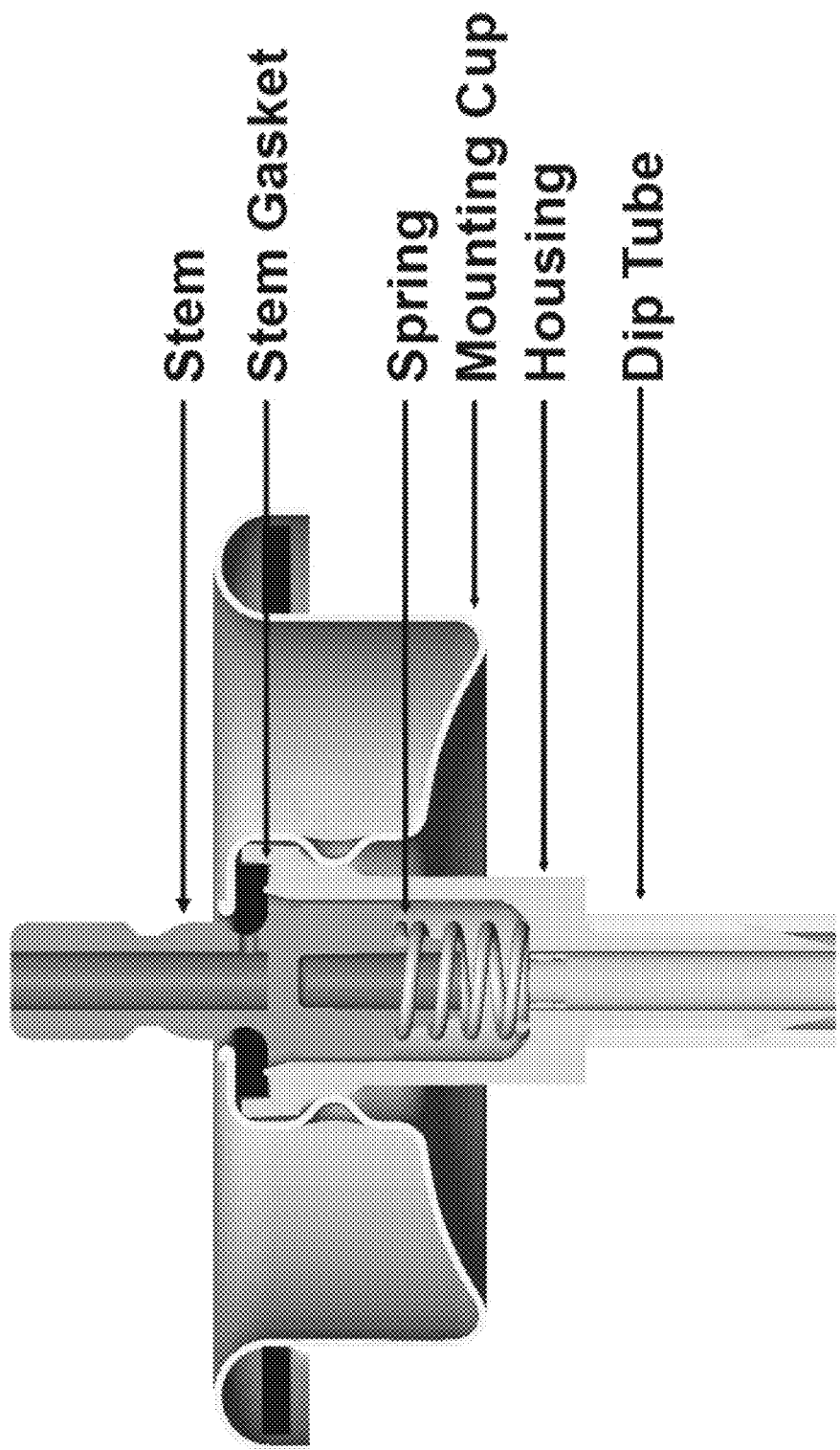
Figure 2:
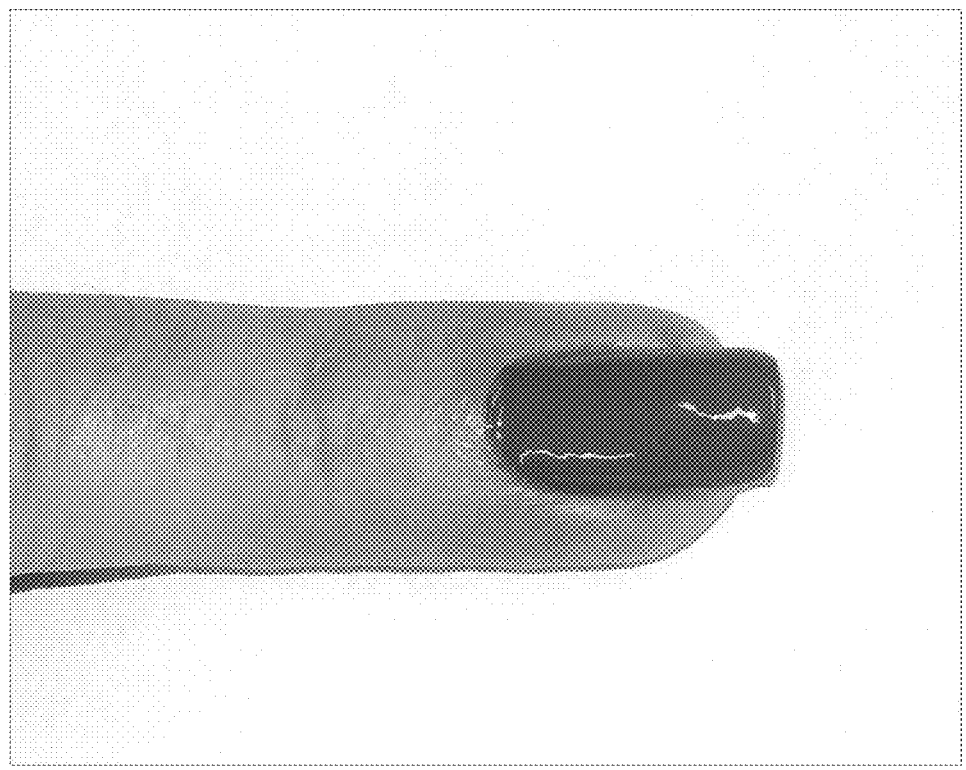
FIG. 2 shows a nail coated with the opaque red nail lacquer.
Figure 3:
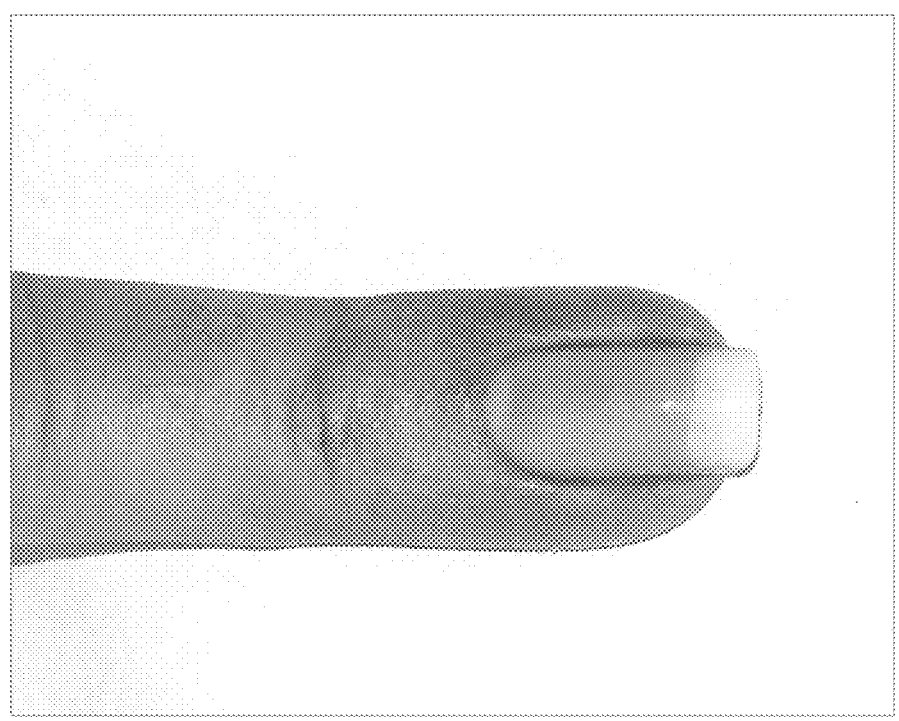
FIG. 3 shows a nail after the opaque red nail lacquer was removed using an acetone-containing aerosolizable composition as prepared according to Example 6 using the acetone-containing solvent composition of Example 1.
Figure 4:
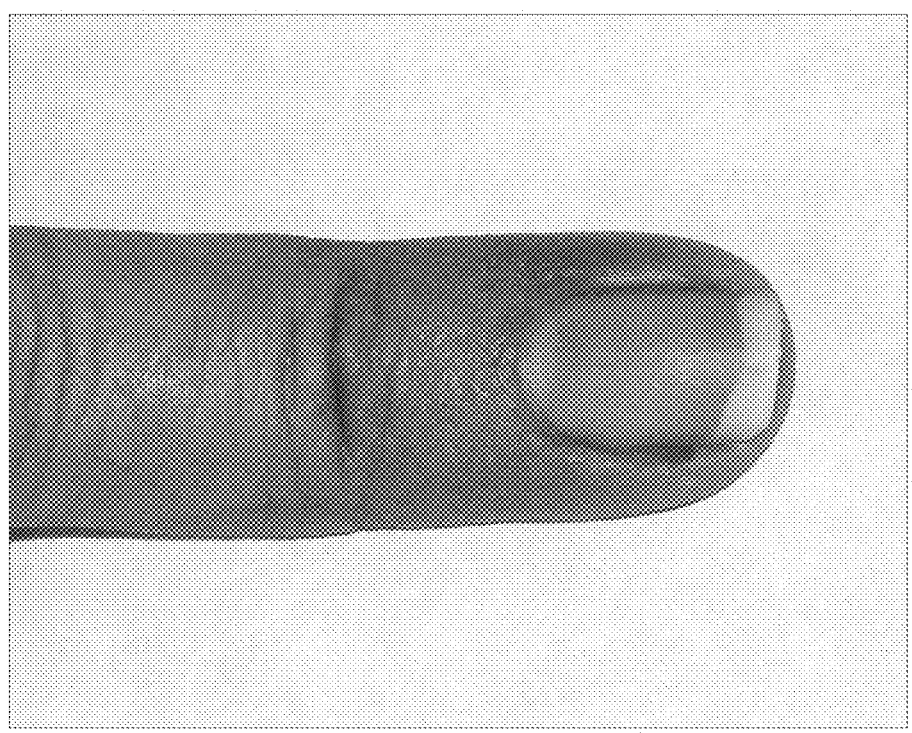
FIG. 4 shows a nail after the opaque red nail lacquer was removed using an acetone-free aerosolizable composition as prepared according to Example 6 using the acetone-free solvent composition of Example 4.

As clearly seen in FIGS. 3 and 4, removing the opaque red nail lacquer from the nail using a composition according to the disclosure does not leave any white/cloudy residue on the nail and/or surrounding skin, and also avoids peeling and chipping of skin and nails.

Figure 5:
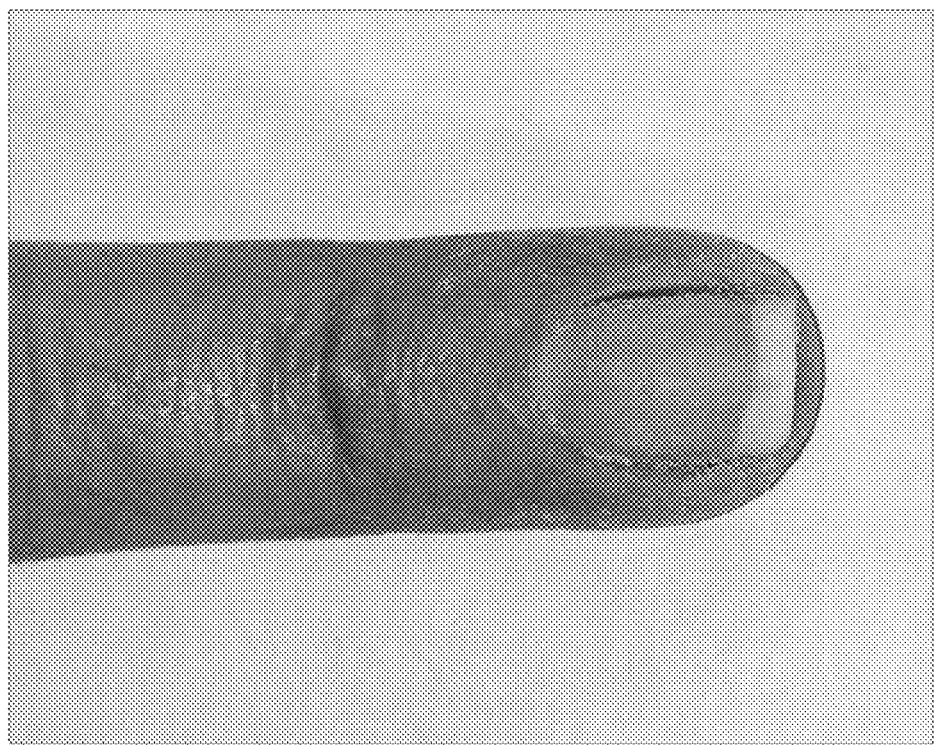
Figure 6A:
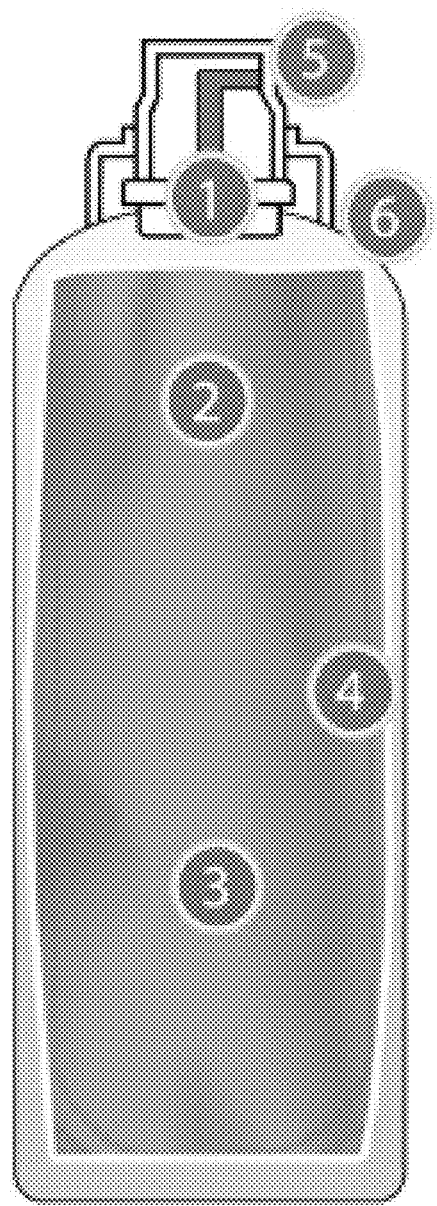

FIG. 5 shows a nail after the opaque red nail lacquer was removed using a regular acetone liquid. As clearly seen in FIG. 5, removing the nail lacquer from the nail using pure acetone leaves white/cloudy residue on the nail, and also leads to drying and peeling of the skin surrounding the nail.

Other Embodiments

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:

1. A solvent composition comprising:
   i) a volatile at least partially water-miscible aprotic organic solvent in an amount from about 65 w/w % to about 85 w/w %;
   ii) a non-volatile water-immiscible aprotic organic solvent in an amount from about 8 w/w % to about 20 w/w %; and
   iii) a non-volatile at least partially water-miscible aprotic organic solvent in an amount from about 8 w/w % to about 20 w/w %;
   wherein the solvent composition does not contain a an estasol dibasic ester solvent selected from the group consisting of dimethyl butanedioate, dimethyl hexanedioate, dimethyl pentanedioate, and a mixture thereof, further comprising:
   iv) oleyl lactate in an amount from about 1 w/w % to about 2 w/w %; and
   v) keratin amino acids and cocoa butter in a combined amount equal to or less than about 1 w/w %.

2. The solvent composition of claim 1, wherein the volatile at least partially water-miscible aprotic organic solvent is a di($C_{1-3}$ alkyl) ketone.

3. The solvent composition of claim 1, wherein the volatile at least partially water-miscible aprotic organic solvent has boiling point in the range from about 50° C. to about 85° C.

4. The solvent composition of claim 1, wherein the volatile at least partially water-miscible aprotic organic solvent is selected from the group consisting of acetone and dioxolane.

5. The solvent composition of claim 1, wherein the non-volatile water-immiscible aprotic organic solvent has boiling point greater than about 100° C.

6. The solvent composition of claim 1, wherein a water solubility of the non-volatile water-immiscible aprotic organic solvent is less than about 2 g per 100 mL of water at 20° C.

7. The solvent composition of claim 1, wherein the non-volatile water-immiscible aprotic organic solvent is a $C_{3-5}$ alkyl acetate.

8. The solvent composition of claim 7, wherein the $C_{3-5}$ alkyl acetate is selected from propyl acetate, n-butyl acetate, isobutyl acetate, tert-butyl acetate, sec-butyl acetate, n-amyl acetate, isoamyl acetate, tert-amyl acetate and sec-amyl acetate.

9. The solvent composition of claim 1, wherein the non-volatile at least partially water-miscible aprotic organic solvent has boiling point greater than about 150° C.

10. The solvent composition of claim 1, wherein the non-volatile at least partially water-miscible aprotic organic solvent is a cyclic carbonate.

11. The solvent composition of claim 10, wherein the cyclic carbonate is selected from ethylene carbonate, trimethylene carbonate and propylene carbonate.

12. The solvent composition of claim 1, wherein:
   the volatile at least partially water-miscible aprotic organic solvent is a di($C_{1-3}$ alkyl) ketone;
   the non-volatile water-immiscible aprotic organic solvent is a $C_{3-5}$ alkyl acetate, and
   the non-volatile at least partially water-miscible aprotic organic solvent is a cyclic carbonate.

13. The composition of claim 12, comprising:
   i) di($C_{1-3}$ alkyl) ketone in an amount from about 70 w/w % to about 80 w/w %;
   ii) $C_{3-5}$ alkyl acetate in an amount from about 10 w/w % to about 15 w/w %; and
   iii) cyclic carbonate in an amount from about 10 w/w % to about 15 w/w %.

14. The solvent composition of claim 1 comprising:
   i) acetone in an amount from about 70 w/w % to about 80 w/w %;
   ii) butyl acetate in an amount from about 10 w/w % to about 15 w/w %; and
   iii) propylene carbonate in an amount from about 10 w/w % to about 15 w/w %.

15. The solvent composition of claim 1, further comprising a humectant selected from the group consisting of: propylene glycol and glycerin.

16. The solvent composition of claim 1, wherein application of the composition for removing a polish from a nail does not leave any white or cloudy residue on the nail.

* * * * *

UNITED STATES PATENT AND TRADEMARK OFFICE
CERTIFICATE OF CORRECTION

PATENT NO.       : 10,085,926 B2
APPLICATION NO.  : 15/645958
DATED            : October 2, 2018
INVENTOR(S)      : Neal Kevin Wallach, Scott Hofmann and Tam Tran It is certified that error appears in the above-identified patent and that said Letters Patent is hereby corrected as shown below:

On the Title Page

Column 2, Item (57) Abstract, Line 1, delete "The present application provides acetone-containing and acetone-free solvent compositions. The compositions may be non-aerosolizable. The compositions may also contain a propellant and be aerosolizable. The aerosolizable compositions may be stored and used in an aerosol container, which can produce a relatively coarse spray containing the aerosolizable composition. In one aspect, the compositions of the present disclosure are cosmetic compositions, e.g., nail polish remover compositions. Also provided are the methods for removing nail polish from a person's nail using the aerosolizable and non-aerosolizable solvent compositions." insert --The present application provides acetone-containing and acetone-free solvent compositions. The compositions may be non-aerosolizable. The compositions may also contain a propellant and be aerosolizable. The aerosolizable compositions may be stored and used in an aerosol container, which can produce a relatively coarse spray containing the aerosolizable composition. In one aspect, the compositions of the present disclosure are cosmetic compositions, e.g., nail polish remover compositions. Also provided are the methods for removing nail polish from a person's nail using the aerosolizable and non-aerosolizable solvent compositions.--.

In the Claims

Column 25, Line 57, Claim 1, delete "a an" insert --an--.

Signed and Sealed this
Nineteenth Day of March, 2019

Andrei Iancu
*Director of the United States Patent and Trademark Office*